United States Patent
Libbus et al.

(10) Patent No.: US 9,764,138 B2
(45) Date of Patent: *Sep. 19, 2017

(54) IMPLANTABLE NEUROSTIMULATOR-IMPLEMENTED METHOD FOR MANAGING TACHYARRHYTHMIA THROUGH VAGUS NERVE STIMULATION

(71) Applicant: CYBERONICS, INC., Houston, TX (US)

(72) Inventors: Imad Libbus, St. Paul, MN (US); Badri Amurthur, Los Gatos, CA (US); Bruce H. KenKnight, Maple Grove, MN (US)

(73) Assignee: CYBERONICS, INC., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/274,919

(22) Filed: Sep. 23, 2016

(65) Prior Publication Data

US 2017/0100592 A1 Apr. 13, 2017

Related U.S. Application Data

(63) Continuation of application No. 13/673,766, filed on Nov. 9, 2012, now Pat. No. 9,452,290.

(51) Int. Cl.
*A61N 1/36* (2006.01)
*A61B 5/0245* (2006.01)
(Continued)

(52) U.S. Cl.
CPC ........ *A61N 1/36114* (2013.01); *A61B 5/0245* (2013.01); *A61B 5/042* (2013.01);
(Continued)

(58) Field of Classification Search
CPC .. A61N 1/362; A61N 1/3621; A61N 1/36114; A61N 1/36117; A61N 1/36535; A61N 1/36542; A61N 1/36053
See application file for complete search history.

(56) References Cited

U.S. PATENT DOCUMENTS 5,330,507 A 7/1994 Schwartz
5,522,854 A 6/1996 Ideker et al.
(Continued)

FOREIGN PATENT DOCUMENTS

WO WO-93/21824 11/1993
WO WO-2010/005482 A1 1/2010

OTHER PUBLICATIONS

US 8,315,702, 11/2012, Chavan et al. (withdrawn)
(Continued)

*Primary Examiner* — George Evanisko
(74) *Attorney, Agent, or Firm* — Foley & Lardner LLP

(57) ABSTRACT

An implantable neurostimulator-implemented method for managing tachyarrhythmias through vagus nerve stimulation is provided. An implantable neurostimulator, including a pulse generator, is configured to deliver electrical therapeutic stimulation in a manner that results in creation and propagation (in both afferent and efferent directions) of action potentials within neuronal fibers of a patient's cervical vagus nerve. Operating modes of the pulse generator are stored. A maintenance dose of the electrical therapeutic stimulation is delivered to the vagus nerve via the pulse generator to restore cardiac autonomic balance through continuously-cycling, intermittent and periodic electrical pulses. A restorative dose of the electrical therapeutic stimulation is delivered to prevent initiation of or disrupt tachyarrhythmia through periodic electrical pulses delivered at higher intensity than the maintenance dose. The patient's normative physiology is monitored via a physiological sen-
(Continued)

sor, and upon sensing a condition indicative of tachyarrhythmia, is switched to delivering the restorative dose to the vagus nerve.

20 Claims, 5 Drawing Sheets

(51) Int. Cl.
    *A61B 5/042*           (2006.01)
    *A61B 5/0456*         (2006.01)
    *A61B 5/0464*         (2006.01)
    *A61B 5/00*            (2006.01)
    *A61N 1/362*          (2006.01)

(52) U.S. Cl.
    CPC .......... *A61B 5/0456* (2013.01); *A61B 5/0464* (2013.01); *A61B 5/4836* (2013.01); *A61B 5/686* (2013.01); *A61N 1/36053* (2013.01); *A61N 1/36139* (2013.01); *A61N 1/3621* (2013.01)

(56) References Cited

U.S. PATENT DOCUMENTS

| | | | |
|---|---|---|---|
| 5,707,400 A | 1/1998 | Terry, Jr. et al. | |
| 5,928,272 A | 7/1999 | Adkins et al. | |
| 5,978,709 A | 11/1999 | Begemann et al. | |
| 6,006,134 A | 12/1999 | Hill et al. | |
| 6,266,564 B1 | 7/2001 | Hill et al. | |
| 6,354,991 B1 | 3/2002 | Gross et al. | |
| 6,449,507 B1 | 9/2002 | Hill et al. | |
| 6,473,644 B1 | 10/2002 | Terry et al. | |
| 6,508,771 B1 | 1/2003 | Padmanabhan et al. | |
| 6,522,926 B1 | 2/2003 | Kieval et al. | |
| 6,600,954 B2 | 7/2003 | Cohen et al. | |
| 6,610,713 B2 | 8/2003 | Tracey | |
| 6,616,624 B1 | 9/2003 | Kieval | |
| 6,622,041 B2 | 9/2003 | Terry, Jr. et al. | |
| 6,652,449 B1 | 11/2003 | Gross et al. | |
| 6,684,105 B2 | 1/2004 | Cohen et al. | |
| 6,690,971 B2 | 2/2004 | Schauerte et al. | |
| 6,712,772 B2 | 3/2004 | Cohen et al. | |
| 6,718,208 B2 | 4/2004 | Hill et al. | |
| 6,838,471 B2 | 1/2005 | Tracey | |
| 6,839,594 B2 | 1/2005 | Cohen et al. | |
| 6,850,801 B2 | 2/2005 | Kieval et al. | |
| 6,862,480 B2 | 3/2005 | Cohen et al. | |
| 6,892,098 B2 | 5/2005 | Ayal et al. | |
| 6,896,651 B2 | 5/2005 | Gross et al. | |
| 6,904,318 B2 | 6/2005 | Hill et al. | |
| 6,907,295 B2 | 6/2005 | Gross et al. | |
| 6,963,773 B2 | 11/2005 | Waltman et al. | |
| 6,963,779 B1 | 11/2005 | Shankar | |
| 6,985,774 B2 | 1/2006 | Kieval et al. | |
| 7,010,345 B2 | 3/2006 | Hill et al. | |
| 7,072,720 B2 | 7/2006 | Puskas | |
| 7,123,961 B1 | 10/2006 | Kroll et al. | |
| 7,136,705 B1 | 11/2006 | Park | |
| 7,139,607 B1 | 11/2006 | Shelchuk | |
| 7,158,832 B2 | 1/2007 | Kieval et al. | |
| 7,184,828 B2 | 2/2007 | Hill et al. | |
| 7,184,829 B2 | 2/2007 | Hill et al. | |
| 7,189,204 B2 | 3/2007 | Ni et al. | |
| 7,218,964 B2 | 5/2007 | Hill et al. | |
| 7,221,979 B2 | 5/2007 | Zhou et al. | |
| 7,225,017 B1 | 5/2007 | Shelchuk | |
| 7,225,019 B2 | 5/2007 | Jahns et al. | |
| 7,237,320 B2 | 7/2007 | Lam | |
| 7,245,967 B1 | 7/2007 | Shelchuk | |
| 7,260,431 B2 | 8/2007 | Libbus et al. | |
| 7,269,457 B2 | 9/2007 | Shafer et al. | |
| 7,277,761 B2 | 10/2007 | Shelchuk | |
| 7,295,881 B2 | 11/2007 | Cohen et al. | |
| 7,305,265 B2 | 12/2007 | Fukui | |
| 7,321,793 B2 | 1/2008 | Ezra et al. | |
| 7,324,853 B2 | 1/2008 | Ayal et al. | |
| 7,336,997 B2 | 2/2008 | Fukui | |
| 7,346,398 B2 | 3/2008 | Gross et al. | |
| 7,387,603 B2 | 6/2008 | Gross et al. | |
| 7,389,149 B2 | 6/2008 | Rossing et al. | |
| 7,395,119 B2 | 7/2008 | Hagen et al. | |
| 7,403,819 B1 | 7/2008 | Shelchuk et al. | |
| 7,418,292 B2 | 8/2008 | Shafer | |
| 7,452,800 B2 | 11/2008 | Sosnowchik et al. | |
| 7,480,532 B2 | 1/2009 | Kieval et al. | |
| 7,481,759 B2 | 1/2009 | Whitehurst et al. | |
| 7,485,104 B2 | 2/2009 | Kieval | |
| 7,493,167 B2 | 2/2009 | Hussein et al. | |
| 7,499,742 B2 | 3/2009 | Bolea et al. | |
| 7,499,747 B2 | 3/2009 | Kieval et al. | |
| 7,499,748 B2 | 3/2009 | Moffitt et al. | |
| 7,502,650 B2 | 3/2009 | Kieval | |
| 7,542,800 B2 | 6/2009 | Libbus et al. | |
| 7,548,780 B2 | 6/2009 | Libbus et al. | |
| 7,551,958 B2 | 6/2009 | Libbus et al. | |
| 7,561,922 B2 | 7/2009 | Cohen et al. | |
| 7,561,923 B2 | 7/2009 | Libbus et al. | |
| 7,570,999 B2 | 8/2009 | Libbus et al. | |
| 7,582,053 B2 | 9/2009 | Gross et al. | |
| 7,584,004 B2 | 9/2009 | Caparso et al. | |
| 7,587,238 B2 | 9/2009 | Moffitt et al. | |
| 7,606,622 B2 | 10/2009 | Reeve | |
| 7,613,511 B2 | 11/2009 | Wu et al. | |
| 7,613,516 B2 | 11/2009 | Cohen et al. | |
| 7,616,990 B2 | 11/2009 | Chavan et al. | |
| 7,617,003 B2 | 11/2009 | Caparso et al. | |
| 7,623,926 B2 | 11/2009 | Rossing et al. | |
| 7,627,384 B2 | 12/2009 | Ayal et al. | |
| 7,628,750 B2 | 12/2009 | Cohen et al. | |
| 7,630,760 B2 | 12/2009 | Libbus et al. | |
| 7,634,315 B2 | 12/2009 | Cholette | |
| 7,634,317 B2 | 12/2009 | Ben-David et al. | |
| 7,640,057 B2 | 12/2009 | Libbus et al. | |
| 7,647,101 B2 | 1/2010 | Libbus et al. | |
| 7,647,114 B2 | 1/2010 | Libbus | |
| 7,650,190 B2 | 1/2010 | Zhou et al. | |
| 7,657,312 B2 | 2/2010 | Pastore et al. | |
| 7,660,628 B2 | 2/2010 | Libbus et al. | |
| 7,664,548 B2 | 2/2010 | Amurthur et al. | |
| 7,668,602 B2 | 2/2010 | Ben-David et al. | |
| 7,672,633 B2 | 3/2010 | Kondoh | |
| 7,672,733 B2 | 3/2010 | Zhou et al. | |
| 7,676,275 B1 | 3/2010 | Farazi et al. | |
| 7,684,866 B2 | 3/2010 | Fowler et al. | |
| 7,689,286 B2 | 3/2010 | Pastore et al. | |
| 7,711,415 B1 | 5/2010 | Farazi et al. | |
| 7,711,421 B2 | 5/2010 | Shafer et al. | |
| 7,734,355 B2 | 6/2010 | Cohen et al. | |
| 7,751,884 B2 | 7/2010 | Ternes et al. | |
| 7,769,442 B2 | 8/2010 | Shafer | |
| 7,769,446 B2 | 8/2010 | Moffitt et al. | |
| 7,778,702 B2 | 8/2010 | Ben-David et al. | |
| 7,778,703 B2 | 8/2010 | Gross et al. | |
| 7,778,711 B2 | 8/2010 | Ben-David et al. | |
| 7,783,353 B2 | 8/2010 | Libbus et al. | |
| 7,797,041 B2 | 9/2010 | Libbus et al. | |
| 7,801,603 B2 | 9/2010 | Westlund et al. | |
| 7,801,604 B2 | 9/2010 | Brockway et al. | |
| 7,801,614 B2 | 9/2010 | Rossing et al. | |
| 7,805,193 B2 | 9/2010 | Libbus et al. | |
| 7,805,203 B2 | 9/2010 | Ben-David et al. | |
| 7,813,805 B1 | 10/2010 | Farazi | |
| 7,813,812 B2 | 10/2010 | Kieval et al. | |
| 7,835,797 B2 | 11/2010 | Rossing et al. | |
| 7,840,266 B2 | 11/2010 | Libbus et al. | |
| 7,840,271 B2 | 11/2010 | Kieval et al. | |
| 7,844,346 B2 | 11/2010 | Cohen et al. | |
| 7,848,812 B2 | 12/2010 | Crowley et al. | |
| 7,848,816 B1 | 12/2010 | Wenzel et al. | |
| 7,869,869 B1 | 1/2011 | Farazi | |
| 7,885,709 B2 | 2/2011 | Ben-David | |
| 7,885,711 B2 | 2/2011 | Ben-Ezra et al. | |

(56) References Cited

U.S. PATENT DOCUMENTS

| | | |
|---|---|---|
| 7,890,185 B2 | 2/2011 | Cohen et al. |
| 7,894,907 B2 | 2/2011 | Cowan et al. |
| 7,904,151 B2 | 3/2011 | Ben-David et al. |
| 7,904,175 B2 | 3/2011 | Scott et al. |
| 7,904,176 B2 | 3/2011 | Ben-Ezra et al. |
| 7,908,008 B2 | 3/2011 | Ben-David et al. |
| 7,916,013 B2 | 3/2011 | Stevenson |
| 7,925,342 B2 | 4/2011 | Amurthur et al. |
| 7,925,352 B2 | 4/2011 | Stack et al. |
| 7,974,693 B2 | 7/2011 | Ben-David et al. |
| 8,005,542 B2 | 8/2011 | Ben-Ezra et al. |
| 8,005,545 B2 | 8/2011 | Ben-David et al. |
| 8,036,745 B2 | 10/2011 | Ben-David et al. |
| 8,060,197 B2 | 11/2011 | Ben-David et al. |
| 8,065,021 B2 | 11/2011 | Gross et al. |
| 8,083,663 B2 | 12/2011 | Gross et al. |
| 8,116,881 B2 | 2/2012 | Cohen et al. |
| 8,131,362 B2 | 3/2012 | Moffitt et al. |
| 8,160,701 B2 | 4/2012 | Zhao et al. |
| 8,160,705 B2 | 4/2012 | Stevenson et al. |
| 8,195,290 B2 | 6/2012 | Brockway et al. |
| 8,224,436 B2 | 7/2012 | Libbus et al. |
| 8,249,711 B2 | 8/2012 | Libbus et al. |
| 8,369,943 B2 | 2/2013 | Shuros et al. |
| 8,386,038 B2 | 2/2013 | Bianchi et al. |
| 8,401,640 B2 | 3/2013 | Zhao et al. |
| 8,417,354 B2 | 4/2013 | Zhang et al. |
| 8,571,654 B2 | 10/2013 | Libbus et al. |
| 8,577,458 B1 | 11/2013 | Libbus et al. |
| 8,600,505 B2 | 12/2013 | Libbus et al. |
| 8,634,921 B2 | 1/2014 | Chavan et al. |
| 8,688,212 B2 | 4/2014 | Libbus et al. |
| 8,918,190 B2 | 12/2014 | Libbus et al. |
| 9,452,290 B2 * | 9/2016 | Libbus ............... A61N 1/36053 |
| 2002/0107553 A1 | 8/2002 | Hill et al. |
| 2003/0018113 A1 | 1/2003 | Nakahama et al. |
| 2003/0040774 A1 | 2/2003 | Terry et al. |
| 2003/0099373 A1 | 5/2003 | Joo et al. |
| 2003/0099377 A1 | 5/2003 | Hanawa |
| 2003/0153954 A1 | 8/2003 | Park et al. |
| 2003/0171781 A1 | 9/2003 | Florio et al. |
| 2004/0110549 A1 | 6/2004 | Pope et al. |
| 2004/0110550 A1 | 6/2004 | Pope et al. |
| 2004/0199210 A1 | 10/2004 | Shelchuk |
| 2004/0210261 A1 | 10/2004 | King et al. |
| 2004/0215265 A1 | 10/2004 | Keizer |
| 2005/0011805 A1 | 1/2005 | Lyons et al. |
| 2005/0049655 A1 | 3/2005 | Boveja et al. |
| 2005/0065553 A1 | 3/2005 | Ezra et al. |
| 2005/0125044 A1 | 6/2005 | Tracey |
| 2005/0131467 A1 | 6/2005 | Boveja |
| 2005/0165465 A1 | 7/2005 | Pianca et al. |
| 2005/0267542 A1 | 12/2005 | David et al. |
| 2006/0015153 A1 | 1/2006 | Gliner et al. |
| 2006/0019764 A1 | 1/2006 | Gegelys |
| 2006/0100668 A1 | 5/2006 | Ben-David et al. |
| 2006/0190053 A1 | 8/2006 | Dobak, III |
| 2006/0206155 A1 | 9/2006 | Ben-David et al. |
| 2006/0253161 A1 | 11/2006 | Libbus et al. |
| 2007/0067004 A1 | 3/2007 | Boveja et al. |
| 2007/0093870 A1 | 4/2007 | Maschino |
| 2007/0179543 A1 | 8/2007 | Ben-David et al. |
| 2007/0213773 A1 | 9/2007 | Hill et al. |
| 2007/0233194 A1 | 10/2007 | Craig |
| 2007/0255320 A1 | 11/2007 | Inman et al. |
| 2007/0276453 A1 | 11/2007 | Hill et al. |
| 2008/0015659 A1 | 1/2008 | Zhang et al. |
| 2008/0021503 A1 | 1/2008 | Whitehurst et al. |
| 2008/0033511 A1 | 2/2008 | Dobak |
| 2008/0051839 A1 | 2/2008 | Libbus et al. |
| 2008/0058874 A1 | 3/2008 | Westlund et al. |
| 2008/0061240 A1 | 3/2008 | Heuft |
| 2008/0091240 A1 | 4/2008 | Ben-David et al. |
| 2008/0132983 A1 | 6/2008 | Cohen et al. |
| 2008/0147140 A1 | 6/2008 | Ternes et al. |
| 2008/0183258 A1 | 7/2008 | Inman |
| 2008/0243196 A1 | 10/2008 | Libbus et al. |
| 2008/0319513 A1 | 12/2008 | Pu et al. |
| 2009/0024186 A1 | 1/2009 | Brockway et al. |
| 2009/0030493 A1 | 1/2009 | Colborn et al. |
| 2009/0118777 A1 | 5/2009 | Iki et al. |
| 2009/0124848 A1 | 5/2009 | Miazga |
| 2009/0149900 A1 | 6/2009 | Moffitt et al. |
| 2009/0248097 A1 | 10/2009 | Tracey et al. |
| 2009/0270953 A1 | 10/2009 | Ecker et al. |
| 2009/0275956 A1 | 11/2009 | Burnes et al. |
| 2010/0010556 A1 | 1/2010 | Zhao et al. |
| 2010/0010603 A1 | 1/2010 | Ben-David et al. |
| 2010/0016919 A1 | 1/2010 | Hill et al. |
| 2010/0042173 A1 | 2/2010 | Farazi et al. |
| 2010/0114197 A1 | 5/2010 | Burnes et al. |
| 2010/0114203 A1 | 5/2010 | Burnes et al. |
| 2010/0114227 A1 | 5/2010 | Cholette et al. |
| 2010/0174341 A1 | 7/2010 | Bolea et al. |
| 2010/0286740 A1 | 11/2010 | Libbus et al. |
| 2010/0331908 A1 | 12/2010 | Farazi |
| 2011/0015692 A1 | 1/2011 | Libbus et al. |
| 2011/0082514 A1 | 4/2011 | Libbus et al. |
| 2011/0098796 A1 | 4/2011 | Ben-David et al. |
| 2011/0224749 A1 | 9/2011 | Ben-David et al. |
| 2011/0257708 A1 | 10/2011 | Kramer et al. |
| 2011/0313488 A1 | 12/2011 | Hincapie Ordonez et al. |
| 2012/0143286 A1 | 6/2012 | Hahn et al. |
| 2012/0172742 A1 | 7/2012 | Arcot-Krishnamurthy et al. |
| 2012/0185007 A1 | 7/2012 | Ziegler et al. |
| 2012/0185010 A1 | 7/2012 | Zhou et al. |
| 2012/0192874 A1 | 8/2012 | Bolea et al. |
| 2012/0271374 A1 | 10/2012 | Nelson et al. |
| 2012/0303080 A1 | 11/2012 | Ben-David et al. |
| 2013/0158616 A1 | 6/2013 | Libbus et al. |
| 2013/0158617 A1 | 6/2013 | Libbus et al. |
| 2013/0158618 A1 | 6/2013 | Libbus et al. |
| 2013/0238047 A1 | 9/2013 | Libbus et al. |
| 2013/0289646 A1 | 10/2013 | Libbus et al. |
| 2014/0025132 A1 | 1/2014 | Libbus et al. |
| 2014/0135862 A1 | 5/2014 | Libbus et al. |
| 2014/0135863 A1 | 5/2014 | Libbus et al. |
| 2014/0135864 A1 | 5/2014 | Libbus et al. |
| 2014/0228905 A1 | 8/2014 | Bolea |
| 2014/0277232 A1 | 9/2014 | Libbus et al. |
| 2015/0073511 A1 | 3/2015 | Libbus et al. |
| 2015/0073512 A1 | 3/2015 | Libbus et al. |
| 2015/0094962 A1 | 4/2015 | Hoegh et al. |
| 2015/0119956 A1 | 4/2015 | Libbus et al. |
| 2015/0119959 A1 | 4/2015 | Libbus et al. |
| 2015/0196762 A1 | 7/2015 | Amurthur et al. |
| 2015/0273214 A1 | 10/2015 | Kenknight et al. |
| 2015/0306394 A1 | 10/2015 | Libbus et al. |
| 2015/0306395 A1 | 10/2015 | Libbus et al. |
| 2015/0321001 A1 | 11/2015 | Libbus et al. |

OTHER PUBLICATIONS

Zhang, et al., "Chronic Vagus Nerve Stimulation Improves Autonomic Control and Attenuates Systemic Inflammation and Heart Failure Progression in a Canine High-Rate Pacing Model," Journal of the American Heart Association, Circ Heart Fail, 2, pp. 692-699 (2009).

Abraham, et al., "Devices in the management of advanced, chronic heart failure," Nature Reviews, vol. 10, pp. 98-110 (Feb. 2013) (Published online Dec. 11, 2012).

Adamson, et al., "Continuous Autonomic Assessment in Patients with Symptomatic Heart Failure: Prognostic Value of Heart Rate Variability Measured by an Implanted Cardiac Resynchronization Device," Circulation, Journal of the American Heart Association, 110, pp. 2389-2394 (2004).

Agostoni, et al., "Functional and Histological Studies of the Vagus Nerve and its Branches to the Heart, Lungs and Abdominal Viscera in the Cat," J. Physiol. 135, pp. 182-205 (1957).

Ajani, et al., "Prevalence of High C-Reactive Protein in Persons with Serum Lipid Concentrations within Recommended Values," Chemical Chemistry, 50:9, pp. 1618-1622 (2004).

(56) References Cited

OTHER PUBLICATIONS

Akiyama, et al., "Effects of right and left vagal stimulation on left ventricular acetylcholine levels in the cat," Acta Physiol Scand, 172, pp. 11-16 (2001).
Anand, et al., "C-Reactive Protein in Heart Failure: Prognostic Value and the Effect of Valsartan," Circulation, Journal of the American Heart Association, 112, pp. 1428-1434 (2005).
Anholt, et al., "Recruitment and blocking properties of the CardioFit stimulation lead," Journal of Neural Engineering, 8, pp. 1-6, (2011).
Ardell, et al.; "Selective vagal innervation of sinoatrial and atrioventricular nodes in canine heart," Am. J. Physiol. 251 (Heart Circ. Physiol. 20), pp. H764-H773 (1986).
Armour, "Cardiac neuronal hierarchy in health and disease," Am J Physiol Regul Integr Comp Physiol, 287, pp. R262-R271 (2004).
Armour, "Myocardial ischaemia and the cardiac nervous system," Cardiovascular Research, 41, pp. 41-54 (1999).
Armour, "The little brain on the heart," Cleveland Clinic Journal of Medicine, vol. 74, supp. 1, pp. S48-S51 (Feb. 2007).
Armour, et al., "Functional anatomy of canine cardiac nerves," Acta anat., 91, pp. 510-528 (1975).
Armour, et al., "Localized myocardial responses to stimulation of small cardiac branches of the vagus," American Journal of Physiology, vol. 228, No. 1 pp. 141-148 (Jan. 1975).
Armour, J.A., "Potential clinical relevance of the 'little brain' on the mammalian heart," Experimental Physiology, vol. 193, No. 2, pp. 165-176 (Feb. 2008). Online Publication Date: Nov. 2, 2007. Available at: http://ep.physoc.org/ content193/2/165.long.
Asala, et al., "An electron microscope study of vagus nerve composition in the ferret," Anat Embryol, 175, pp. 247-253 (1986).
Aukrust, et al., "Inflammatory and anti-inflammatory cytokines in chronic heart failure: Potential therapeutic implications," Annals of Medicine, 37, pp. 74-85 (2005).
Author Unknown, "Nerve fiber—Types and Function," www.boddunan.com Available at www.boddunan.com/education/20-medicine-a-surgery/12730-nerver-fiber- types-and-function.html (Apr. 19, 2010).
Author Unknown, American Diabetes Association, "Standards of Medical Care in Diabetes—2012," Diabetes Care, vol. 35, supplement 1, pp. S11-S63 (Jan. 2012).
Author Unknown, Staff of Adinstruments, "Principles of Nerve Stimulation," Application Note, ADInstruments (Apr. 2002).
Bae, et al., "Gliosis in the Amygdala Following Myocardial Infarction in the Rat," J Vet Med Sci, 72(8), pp. 1041-1045 (2010).
Bernik, et al., "Pharmacological Stimulation of the Cholinergic Antiinflammatory Pathway," J. Exp. Med, vol. 195, No. 6, pp. 781-788 (Mar. 18, 2002).
Berthoud, et al., "Functional and chemical anatomy of the afferent vagal system," Autonomic Neuroscience: Basic and Clinical, 85, pp. 1-17 (2000).
Bhagat, et al., "Differential Effect of Right and Left Vagal Stimulation on Right and Left Circumflex Coronary Arteries," S A Medical Journal, 50, pp. 1591-1594 (1976).
Biasucci, et al., "Elevated Levels of C-Reactive Protein at Discharge in Patients with Unstable Angina Predict Recurrent Instability," Circulation, Journal of the American Heart Association, 99, pp. 855-860 (1999).
Bibevski, et al., "Evidence for impaired vagus nerve activity in heart failure," Heart Fail Rev, 16, pp. 129-135 (2011).
Bibevski, et al., "Ganglionic Mechanisms Contribute to Diminished Vagal Control in Heart Failure," Circulation, Journal of the American Heart Association, 99, pp. 2958-2963 (1999).
Bilgutay, et al., "Vagal Tuning a new concept in the treatment of supraventricular arrhythmias, angina pectoris, and heart failure," Journal of Thoracic and Cardiovascular Surgery, vol. 56, No. 1, pp. 71-82 (Jul. 1968).
Binkley, et al., "Parasympathetic Withdrawal Is an Integral Component of Autonomic Imbalance in Congestive Heart Failure: Demonstration in Human Subjects and Verification in a Paced Canine Model of Ventricular Failure," JACC, vol. 18, No. 2, pp. 464-472 (Aug. 1991).
Bois, et al., "Mode of action of bradycardic agent, S 16257, on ionic currents of rabbit sinoatrial node cells," Abstract, British Journal of Pharmacology, 118(4):1051-7 (1996).
Bonaz, et al., "Vagus nerve stimulation: From epilepsy to the cholinergic anti-inflammatory pathway," Neurogastroenterology & Motility, pp. 1-14 (2013).
Borggrefe, et al., "Vagal Stimulation Devices," ESC Congress 2010 (2010).
Borovilkova, et al., "Vagus nerve stimulation attenuates the systemic inflammatory response to endotoxin," Nature, vol. 405, pp. 458-462 (May 25, 2000).
Brack, et al., "Mechanisms underlying the autonomic modulation of ventricular fibrillation initiation—tentative prophylactic properties in vagus nerve stimulation on malignant arrhythmias in heart failure," Heart Fail Rev (Published online Jun. 8, 2012).
Bronzino, "Biomedical Engineering Fundamentals," CRC Press, Chapter 30, pp. 30-10-30-15 (Apr. 2006).
Buschman, et al., "Heart Rate Control Via Vagus Nerve Stimulation," Neuromodulation, vol. 9, No. 3, pp. 214-220 (2006).
Butterwick, et al., "Tissue Damage by Pulsed Electrical Stimulation," IEEE Transactions on Biomedical Engineering, vol. 54, No. 12, pp. 2261-2267 (Dec. 2007).
Calkins, et al., "Comparison of Responses to Isoproterenol and Epinephrine During Head-Up Tilt in Suspected Vasodepressor Syncope," The American Journal of Cardiology, vol. 67 pp. 207-209 (Jan. 15, 1991).
Chapleau, et al., "Methods of assessing vagus nerve activity and reflexes," Heart Fail Rev, 16, pp. 109-127 (2011).
Chen, et al., "National and Regional Trends in Heart Failure Hospitalization and Mortality Rates for Medicare Beneficiaries, 1998-2008," JAMA, vol. 306, No. 15 (Oct. 19, 2011).
Chen, et al., "Role of Atrial Electrophysiology and Autonomic Nervous System in Patients with Supraventricular Tachycardia and Paroxysmal Artrial Fibrillation," J Am Coll Cardiol, vol. 32, No. 3, pp. 732-738 (Sep. 1998).
Cheng, et al., "Long-term Outcomes in Individuals with Prolonged PR Interval or First-Degree Atrioventricular Block," JAMA, vol. 301, No. 24 pp. 2571-2577 (Jun. 24, 2009).
Chiou, et al., "Effects of Continuous Enhanced Vagal Tone and Dual Atrioventricular Node and Accessory Pathways," Circulation, Journal of the American Heart Association, 107, pp. 2583-2588 (2003).
Cohen, et al., "Histopathology of the stimulated Vagus nerve: Primum non nocere," Heart Fail Rev, 16, pp. 163-169 (2011).
Colombo, et al., "Comparison between spectral analysis and the phenylephrine methods for the assessment of baroreflex sensitivity in chronic heart failure," Clinical Science, 97, pp. 503-513 (1999).
Cryan, et al., "Animal models and mood disorders: recent developments," Current Opinion in Psychiatry, 20, pp. 1-7 (2007).
Das, "Vagal nerve stimulation in prevention and management of coronary heart disease," World J. Cardiol, 3(4), pp. 105-110 (Apr. 26, 2011).
De Castro, et al., "Parasympathetic-mediated atrial fibrillation during tilt test associated with increased baroreflex sensitivity," The European Society of Cardiology, Europace, 8, pp. 349-351 (2006).
De Ferrari et al., Chronic Vagus Nerve Stimulation: A New and Promising Therapeutic Approach for Chronic Heart Failure, European Heart Journal, vol. 32, Oct. 28, 2010, pp. 847-855.
De Ferrari, et al., "Baroreflex Sensitivity Predicts Long-Term Cardiovascular Mortality After Myocardial Infarction Even in Patients with Preserved Left Ventricular Function," Journal of the American College of Cardiology, vol. 50, No. 24, pp. 2285-2290 (2007).
De Ferrari, et al., "Chronic Vagal Stimulation in Patients with Congestive Heart Failure," 31st Annual International Conference of the IEE EMBS (2009).
De Ferrari, et al., "Vagus nerve stimulation: from pre-clinical to clinical application: challenges and future directions," Heart Fail Rev, 16, pp. 195-203 (2011) (Published Online Dec. 17, 2010).
De Jonge, et al., "Stimulation of the vagus nerve attenuates macrophage activation by activating the Jak2-STAT3 signaling pathway," Nature Immunology, val. 6, No. 8, pp. 844-852 (Aug. 2005).
De Jonge, et al., "Stimulation of the vagus nerve attenuates macrophage activation by activating the Jak2-STAT3 signaling pathway," Nature Immunology, vol. 6, No. 8, pp. 844-852 (Aug. 2005).

(56) References Cited

OTHER PUBLICATIONS

Desai, et al., "Pharmacologic modulation of parasympathetic activity in heart failure," Heart Fail Rev, 16, pp. 179-193 (Published online: Oct. 6, 2010) (2011).
Dickerson, et al., "Parasympathetic neurons in the cranial medial ventricular fat pad on the dog heart selectively decrease ventricular contractility," Journal of the Autonomic Nervous System, 70, pp. 129-141 (1998).
Dunlap, et al., "Mechanisms of altered vagal control in heart failure: influence of muscarinic receptors and acetylcholinesterase activity," Am J Physiol Heart Gire Physiol, 285, pp. H1632-H1640 (Jun. 26, 2003).
Elsenbruch, et al., "Heart Rate Variability During Waking and Sleep in Healthy Males and Females," Sleep, vol. 22, No. 8, pp. 1067-1071 (1999).
Euler, et al., "Acetylcholine release by a stimulus train lowers atrial fibrillation threshold," Am. J Physiol. 253 (Heart Gire. Physiol, 22), pp. H863-H868 (1987).
Evans, et al., "Histological and functional studies on the fibre composition of the vagus nerve of the rabbit," Journal of Anatomy, 130, pp. 139-151 (1954).
Fallen, "Vagal Afferent Stimulation as a Cardioprotective Strategy? Introducing the Concept," A.N.E., vol. 10, No. 4 (Oct. 2005).
Fan, et al., "Transvenous vagus nerve stimulation: A potential heart failure therapy is feasible in humans," JACC, vol. 55, issue 10A, pp. E152-E153 (2010).
Fazan, et al., "Diabetic Peripheral Neuropathies: A Morphometric Overview," Int. J. Morphol, 28(I), pp. 51-64 (2010).
Feinauer, et al., "Ouabain enhances release of acetylcholine in the heart evoked by unilateral vagal stimulation," Arch Pharmacol, 333, pp. 7-12 (1986).
Fonarow, et al., "Incremental Reduction in Risk of Death Associated with Use of Guideline-Recommended Therapies in Patients with Heart Failure: A Nested Case-Control Analysis of Improve HF," J Am Heart Assoc, 1, pp. 16-26 (2012).
Ford, et al., "The effects of electrical stimulation of myelinated and non-myelinated vagal fibres on heart rate in the rabbit," J. Physiol. 380, pp. 341-347 (1986).
Furukawa, et al., "Effects of Verapamil, Zatebradine, and E-4031 on the Pacemaker Location and Rate in Response to Sympathetic Stimulation in Dog Hearts," The Journal of Pharmacology and Experimental Therapeutics, vol. 289, No. 3, pp. 1334-1342 (1999).
Furukawa, et al., "Selective inhibition by zatebradine and discrete parasympathetic stimulation of the positive chronotropic response to sympathetic stimulation in anesthetized dogs," Abstract, Journal of Pharmacology & Experimental Therapeutics, 272(2):744-9 (1995).
Gatti, et al., "Can neurons in the nucleus ambiguous selectively regulate cardiac rate and atrio-ventricular conduction?" Journal of the Autonomic Nervous System, 57, pp. 123-127 (1996).
Gatti, et al., "Vagal control of left ventricular contractility is selectively mediated by a cranioventricular intracardiac ganglion in the cat," Journal of the Autonomic Nervous System, 66, pp. 138-144 (1997).
Gibbons, et al., "Neuromodulation targets intrinsic cardiac neurons to attenuate neuronally mediated atrial arrhythmias," Am J Physiol Regul Integr Comp Physiol 302: R357-R364 (2012) (First published Nov. 16, 2011).
Gottdiener, et al., "Predictors of Congestive Heart Failure in the Elderly: The Cardiovascular Heath Study," Journal of the American College of Cardiology, vol. 35, No. 6, pp. 1628-1637 (2000).
Gray, et al., "Parasympathetic control of the Heart. II. A novel interganglionic intrinsic cardiac circuit mediates neural control of heart rate," J. Appl Physiol, 96, pp. 2273-2278 (2004).
Gray, et al., "Parasympathetic control of the Heart. III. Neuropeptide Y-immunoreactive nerve terminals synapse on three populations of negative chronotropic vagal preganglionic neurons," J. Appl Physiol, 96, pp. 2279-2287 (2004).

Grill, "Chapter 14—Principles of Electric Field Generation for Stimulation of the Central Nervous System," Neuromodulation, Academic Press (2009).
Guilleminault, et al., "Cyclical Variation of the Heart Rate in Sleep Apnea Syndrome," The Lancet, pp. 126-131 (Jan. 21, 1984).
Hardwick, et al., "Chronic myocardial infarction induces phenotypic and functional remodeling in the guinea pig cardiac plexus," Am J Physiol Regulatory Integrative Comp Physiol, 295, pp. 1926-1933 (2008).
Hardwick, et al., "Remodeling of the guinea pig intrinsic cardiac plexus with chronic pressure overload," Am J Physiol Regulatory Integrative Comp Physiol, 297, pp. 859-866 (2009).
Hauptman, et al., "The vagus nerve and autonomic imbalance in heart failure: past, present, and future," Heart Fail Rev, 16, pp. 97-99 (2011).
Hellyer, et al., "Autonomic nerve activity and blood pressure in ambulatory dogs," Heart Rhythym, vol. 11(2), pp. 307-313 (Feb. 2014).
Hirooka, et al., "Imbalance of central nitric oxide and reactive oxygen species in the regulation of sympathetic activity and neural mechanisms of hypertension," Am J Physiol Regulatory Integration Comp Physiol, 300, pp. 818-826 (2011).
Hoffman, et al., "Vagus Nerve Components," Anat Rec, 127, pp. 551-568 (1957).
Hu, et al., "Role of sympathetic nervous system in myocardial ischemia injury: Beneficial or deleterious?" Letters to the Editor, Elsevier Ireland Ltd. (Mar. 27, 2012).
Hua, et al., "Left vagal stimulation induces dynorphin release and suppresses substance P release from the rat thoracic spinal cord during cardiac ischemia," Am J Physiol Regulatory Integration Comp Physiol, 287, pp. 1468-1477 (2004).
Huston, et al., "Splenectomy inactivates the cholinergic antiinflammatory pathway during lethal endotoxemia and polymicrobial sepsis," J. Exp. Med, vol. 203, No. 7 pp. 1623-1628 (Jun. 19, 2006).
Huston, et al., "Transcutaneous vagus nerve stimulation reduces serum high mobility group box 1 levels and improves survival in murine sepsis," Grit Care Med, vol. 35, No. 12, pp. 2762-2768 (2007).
Ingemansson, et al., "Autonomic modulation of the atrial cycle length by the head up tilt test: non-invasive evaluation in patients with chronic atrial fibrillation," Heart, 80, pp. 71-76 (1998).
Ito, et al., "Efferent sympathetic and vagal innervation of the canine right ventricle," Circulation, Journal of the American Heart Association, vol. 90, pp. 1469-1468 (1994).
Jacques, et al., "Spinal Cord Stimulation Causes Potentiation of Right Vagus Nerve Effects on Atrial Chronotropic Function and Repolarization in Canines," Journal of Cardiovascular Electrophysiology, vol. 22, No. 4, pp. 440-447 (Apr. 2011).
Jaenisch, et al., "Respiratory muscle training improves baroreceptor sensitivity, decrease sympathetic tonus and increase vagal effect in rats with heart failure," European Heart Journal, 32 (Abstract Supplement, pp. 976 (2011).
Jammes, et al., "Afferent and efferent components of the bronchial vagal branches in cats," Journal of the Autonomic Nervous System, 5, pp. 165-176 (1982).
Janabi, et al., "Oxidized LDL-Induced NF-kB Activation and Subsequent Expression of Proinflammatory Genes are Defective in Monocyte-Derived Macrophages from CD36-Deficient Patients," Arterioscler Thromb Vase Biol., 20:1953-1960 (2000).
Janse, et al., "Effects of unilateral stellate ganglion stimulation and ablation on electrophysiologic changes induced by acute myocardial ischemia in dogs," Circulation, Journal of the American Heart Association, 72, pp. 585-595 (1985).
Jessup; et al., "2009 Focused Update: ACCF/AHA Guidelines for the Diagnosis and Management of Heart Failure in Adults," Circulation, Journal of the American Heart Association, vol. 119, pp. 1977-2016 (2009).
Johnson, et al., "Parasympathetic control of the heart. I. An interventriculo-septal ganglion is the major source of the vagal intracardiac innervation of the ventricles," J Appl Physiol, 96, pp. 2265-2272 (2004).
Kakinuma, et al., "Cholinoceptive and cholinergic properties of cardiomyocytes involving an amplification mechanism for vagal

(56) References Cited

OTHER PUBLICATIONS efferent effects in sparsely innervated ventricular myocardium," FEBS Journal, 276, pp. 5111-5125 (2009).
Kalman, "Specific effects of zatebradine on sinus node function: suppression of automaticity, prolongation of sinoatrial conduction and pacemaker shift in the denervated canine heart," Abstract, Journal of Pharmacology & Experimental Therapeutics, 272(1):85-93 (1995).
Kaneko, et al., "C-Reactive Protein in Dilated Cardiomyopathy," Cardiology, 91, pp. 215-219 (1999).
Katare, et al., "Vagal nerve stimulation prevents reperfusion injury through inhibition of opening of mitochondrial permeability transition pore independent of bradycardiac effect," The Journal of Thoracic and Cardiovascular Surgery, vol. 137, No. 1, pp. 223-231 (2009).
Katz, et al., "Diseases of the heart in the Works of Hippocrates," Br Heart J, 24, pp. 257-264 (1962).
Kawada, et al., "High-frequency dominant depression of peripheral vagal control of heart rate in rats with chronic heart failure," Acta Physiol 207, 494-502 (2013).
Kawada, et al., "Vagal stimulation suppresses isschemia-induced myocardial interstitial norepinephrine release," Life Sciences, 78, pp. 882-887 (2006).
Kawashima, "The autonomic nervous system of the human heart with special reference to its origin, course, and peripheral distribution," Anat Embryol, 209, pp. 425-438 (2005).
Klein et al., "Vagus nerve stimulation: A new approach to reduce heart failure," Cardiology Journal, vol. 17, iss. 6, pp. 638-643 (2010).
Kliks, et al., "Influence of Sympathetic Tone on Ventricular Fibrillation Threshold During Experimental Coronary Occlusion," The American Journal of Cardiology, vol. 36, pp. 45-49 (Jul. 1975).
Kolman, et al., "The effect of vagus nerve stimulation upon vulnerability of the canine ventricle: role of sympathetic-parasympathetic interactions," Journal of the American Heart Association, 52, pp. 578-585 (1975).
Kong, et al., "Optimizing the Parameters of Vagus Nerve Stimulation by Uniform Design in Rats with Acute Myocardial Infarction," PLOS One, vol. 7, issue 11 (Nov. 2012).
Koopman, et al., "Pilot study of stimulation of the cholinergic anti-inflammatory pathway with an implantable vagus nerve stimulation device in patients with rheumatoid arthritis," Abstract (2012).
Kulbertus, et al., ed., "Neurocardiology," Futura Publishing Co., pp. 13 ("Anatomy of the Cardiac Efferent Innvervation"); 61-63 ("Autonomic Neural Control"); 87, 89, 92-93 ("Sympathetic-Parasympathetic Interactions"); 183, 187 ("Parasympathetic Nervous System"); 104 (1988).
La Rovere, et al., "Baroreflex Sensitivity and Heart Rate Variability in the Identification of Patients at Risk for Life-Threatening Arrhythmias: Implications for Clinical Trials," Circulation, Journal of the American Heart Association, 103, pp. 2072-2077 (2001).
Lane, et al., "Prediction and Prevention of Sudden Cardiac Death in Heart Failure," Heart, 91, pp. 674-680 (2005).
Lechat, et al., "Heart rate and Cardiac Rhythm Relationships with Bisoprolol Benefit in Chronic Heart Failure in CIBIS II Trial," Circulation, Journal of American Heart Association, 103, pp. 1428-1433 (2001).
Lewis, et al., "Vagus nerve stimulation decreases left ventricular contractility in vivo in the human and pig heart," Journal of Physiology, 534, pp. 547-552 (2001).
Li et al., "Vagal Nerve Stimulation Markedly Improves Long-Term Survival After Chronic Heart Failure in Rats," Circulation: Journal of the American Heart Association, vol. 109, iss. 1, pp. 120-124 (Jan. 2004). Online publication date: Dec. 8, 2003.
Li, et al., "Early vagal stimulation markedly prevented cardiac dysfunction in rats after acute myocardial infarction in addition to suppressing arrhythmic death," European Heart Journal, 32 (Abstract Supplement), pp. 297-298 (2011).
Li, et al., "Inflammatory cytokines and nitric oxide in heart failure and potential modulation by vagus nerve stimulation," Heart Fail Rev, 16, pp. 137-145 (2011).
Li, et al., "Low-Level Vagosympathetic Stimulation. A Paradox and Potential New Modality for the Treatment of Focal Atrial Fibrillation," Gire Arrhythm Electrophysiol, Journal of American Heart Association, 2, pp. 645-651 (2009).
Li, et al., "Restoration of vagal tone by donepezil, on top of losartan treatment, markedly suppresses ventricular dysfunction and improves long-term survival in chronic heart failure rats," European Heart Journal, 32 (Abstract Supplement), pp. 642 (2011).
Li, et al., "Vagal nerve Stimulation Markedly Improves Long-Term Survival After Chronic Heart Failure in Rats," Circulation, Journal of the American Heart Association, 109, pp. 120-124 (2004).
Libby, et al., "Inflammation and Atherosclerosis," Circulation, Journal of the American Heart Association, 105, pp. 1135-1143 (2002).
Liu, et al., "Differing sympathetic and vagal effects on atrial fibrillation in dogs: role of refractoriness heterogeneity," Am. J. Physiol. 273 (Heart Gire. Physiol. 42), pp. H805-H816 (1997).
Lo, et al., "Paradoxical long-term proarrhythmic effects after ablating the 'head station' ganglionated plexi of the vagal innervation to the heart," Heart Rhythm, vol. 10, No. 5, pp. 751-757 (May 2013).
Lohmeier, et al., "Prolonged Activation of the Baroreflex Produces Sustained Hypotension," Hypertension, Journal of the American Heart Association, 43, pp. 306-311 (2004).
Lu, et al., "Vagal nerve stimulation protects cardiac injury by attenuating mitochondria) dysfunction in a murine burn injury model," J. Cell. Mol. Med., vol. 17, No. 5, pp. 664-671 (2013).
Ma, et al., "Analysis of afferent, central, and efferent components of the baroreceptor reflex in mice," Am J Physiol Regulatory Integration Comp Physiol, 283, pp. 1033-1040 (2002).
Maj, et al., "P5775: Autonomic imbalance and circulating androgens and estrogens in men with systolic heart failure," European Heart Journal, 32 (Abstract Supplement), pp. 1090 (2011).
Malkin, et al., "Life-saving or life-prolonging? Interpreting trial data and survival curves for patients with congestive heart failure," The European Journal of Heart Failure, 7, pp. 143-148 (2005).
Mann, "Chapter 12—Peripheral Nerves," The Nervous System in Action, michaeldmann.net/mannl2.html, (Jul. 2011).
Mann, "Inflammatory Mediators and the Failing Heart. Past, Present, and the Foreseeable Future," Circ Res., 91, pp. 988-998 (2002).
Mann, "Stress-Activated Cytokines and the Heart: From Adaptation to Maladaptation," Annu. Rev. Physiol., 65, pp. 81-101 (2003).
Martin-Portugues, et al., "Histopathologic features of the vagus nerve after electrical stimulation in swine," Histol Histopathol, 20, pp. 851-856 (2005).
Martins, et al., "Distribution of Local Repolarization Changes Produced by Efferent Vagal Stimulation in the Canine Ventricles," JACC, vol. 2, No. 6, pp. 1191-1199 (Dec. 1983).
Massari, et al., "Neural control of left ventricular contractility in the dog heart: synaptic interactions of negative inotropic vagal preganglionic neurons in the nucleus ambiguus and tyrosine hydroxylase immunoreactive terminals," Brain Research, 802, pp. 205-220 (1998).
May, et al., "P564: Long-term prediction of all-cause mortality in diabetic autonomic neuropathy: simple function tests or 24-hour heart rate variability (HRV)?" European Heart Journal, 32 (Abstract Supplement), pp. 64 (2011).
Mei, et al., "The Composition of the Vagus Nerve of the Cat," Cell Tissue Res., 209, pp. 423-431 (1980).
Merrill, et al., "Electrical stimulation of excitable tissue: design of efficacious and safe protocols," Journal of Neuroscience Methods, 141, pp. 171-198 (2005).
Mortara, et al., "Arterial Baroreflex Modulation of Heart Rate in Chronic Heart Failure," Circulation, Journal of the American Heart Association, vol. 96, No. 10, pp. 3450-3458 (Nov. 18, 1997).
Murakawa, et al., "Effect of Cervical Vagal Nerve Stimulation on Defibrillation Energy," Jpn Heart J, 44, pp. 91-100 (Jan. 2003).
Naito, "Effects of zatebradine and propranolol on canine ischemia and reperfusion-induced arrhythmias," European Journal of Pharmacology, 388, pp. 171-176 (2000).
Nakajima, et al., "Autonomic Control of the Location and Rate of the Cardiac Pacemaker in the Sinoatrial Fat Pad of Parasympatheti-

(56) References Cited

OTHER PUBLICATIONS cally Denervated Dog Hearts," Journal of Cardiovascular Electrophysiology, vol. 13, No. 9 pp. 896-901 (Sep. 2002).
Nearing, et al., "Crescendo in Depolarization and Repolarization Heterogeneity Heralds Development of Ventricular Tachycardia in Hospitalized Patients with Decompensated Heart Failure," Circulation Arrhythmia and Electrophysiology, Journal of the American Heart Association, 5, pp. 84-90 (2012).
Nihei, et al., "Decreased Vagal Control Over Heart Rate in Rats with Right-Sided Congestive Heart Failure—Downregulation of Neuronal Nitric Oxide Synthase," Oirc J, 69, pp. 493-499 (2005).
Ninomiya, "Direct Evidence of Nonuniform Distribution of Vagal Effects on Dog Atria," Circulation Research, vol. XIX, pp. 576-583 (Sep. 1966).
Nolan, et al., "Prospective Study of Heart Rate Variability and Mortality in Chronic Heart Failure: Results of the United Kingdom Heart Failure Evaluation and Assessment of Risk Trial (UK-Heart)," Circulation, Journal of the American Heart Association, 98, pp. 1510-1516 (1998).
Ochoa, et al., "P2497: Effects of insulin resistance on resting heart rate, baroreflex sensitivity and indices of autonomic cardiovascular modulation in individuals with high blood pressure levels," European Heart Journal, 32 (Abstract Supplement, pp. 431-432 (2011).
Ogawa, et al., "Left Stellate Ganglion and Vagal Nerve Activity and Cardiac Arrhythmias in Ambulatory Dogs with Pacing-Induced Congestive Heart Failure," Journal of the American College of Cardiology, vol. 50, No. 4, pp. 335-444 (2007).
Okada, et al., "Cyclic Stretch Upregulates Production of Interleukin-8 and Monocyte Chemotactic and Activating Factor/Monocyte Chemoattractant Protein-1 in Human Endothelial Cells," Arterioscler Thromb Vase Biol., 18, pp. 894-901 (1998).
Oliveira, et al., "Effects of vagal stimulation on induction and termination of atrial fibrillation in an in vivo rabbit heart model," Rev Port Cardiol, 29(03), pp. 375-389 (2010).
Olshansky et al., "Parasympathetic Nervous System and Heart Failure: Pathophysiology and Potential Implications for Therapy," Circulation: Journal of the American Heart Association, vol. 118, iss. 8, pp. 863-871 (Aug. 2008).
Onkka, et al., "Sympathetic nerve fibers and ganglia in canine cervical vagus nerves: Localization and quantitation," Heart Rhythm, vol. 10, No. 4, pp. 585-591 (Apr. 2013).
Ordelman, et al., "Selectivity for Specific Cardiovascular Effects of Vagal Nerve Stimulation with a Multi-Contact Electrode Cuff," IEEE, pp. 1-6 (2011).
Packer, et al., "Effect of Carvedilol on Survival in Severe Chronic Heart Failure," The New England Journal of Medicine, vol. 344, No. 22, pp. 1651-1658 (May 31, 2001).
Pavlov, et al., "Central muscarinic cholinergic regulation of the systemic inflammatory response during endotoxemia," PNAS, vol. 103, No. 13, pp. 5219-5223 (Mar. 28, 2006).
Pavlov, et al., "Controlling inflammation: the cholinergic anti-inflammatory pathway," Biochemical Society Transactions, vol. 34, part 6, pp. 1037-1040 (2006).
PCT Application No. PCT/U52013/068541, Search Report and Written Opinion dated Jan. 7, 2014.
PCT Application No. PCT/US2012/068205, Search Report and Written Opinion dated Feb. 8, 2013, 15 pages.
PCT Application No. PCT/US2012/068211, Search Report and Written Opinion dated Jun. 13, 2013.
PCT Application No. PCT/US2012/068213, Search Report and Written Opinion dated Mar. 15, 2013, 11 pages.
PCT Application No. PCT/US2012/068223, Search Report and Written Opinion dated Apr. 3, 2013, 11 pages.
PCT Application No. PCT/US2013/021964, Search Report and Written Opinion dated Jul. 25, 2013, 9 pages.
PCT Application No. PCT/US2013/050390, Search Report and Written Opinion dated Nov. 5, 2013.
PCT Application No. PCT/US2014/024827, Search Report and Written Opinion dated Nov. 11, 2014, 18 pages.
PCT Application No. PCT/US2015/020116, Search Report and Written Opinion dated Jul. 6, 2015, 12 pages.
Peckham, et al., "Chapter 18—Implantable Neural Stimulators," Neuromodulation, Academic Press (2009).
Pina, et al., "The Predictive Value of Biomarkers in Heart Failure," Medscape Education Cardiology, Available at http://www.medscape.org/viewarticle/765328 (CME Released: Jun. 15, 2012).
Pitzalis, et al., "Comparison Between Noninvasive Indices of Baroreceptor Sensitivity and the Phenylephrine Method in Post-Myocardial Infarction Patients," Circulation, Journal of the American Heart Association, 97, pp. 1362-1367 (1998).
Poole-Wilson, "Relation of Pathophysiologic Mechanisms to Outcome in Heart Failure," JACC, vol. 22, No. 4 (supplement A), pp. 22A-29A (Oct. 1993).
Pye, et al., "Study of serum C-reactive protein concentration in cardiac failure," Br Heart J, 63, pp. 228-230 (1990).
Rademacher, et al., "P5878: Multidimensional halter-based analysis of cardiac autonomic regulation predicts early AF recurrence after electrical cardioversion," European Heart Journal, 32 (Abstract Supplement), pp. 1116-1117 (2011).
Randall, et al., "Regional vagosympathetic control of the heart," American Journal of Physiology, vol. 227, No. 2, pp. 444-452 (1974).
Randall, et al., "Selective Vagal Innervation of the Heart," Annals of Clinical and Laboratory Science, vol. 16, No. 3, pp. 198-208 (1986).
Raymond, et al., "Elevated interleukin-6 levels in patients with asymptomatic left ventricular systolic dysfunction," American Heart Journal, vol. 141, No. 3, pp. 435-438 (Mar. 2001).
Rhee, et al., "Effects of suprathreshold vagal stimulation on stellate ganglion nerve activity in ambulatory dogs," 33rd Annual Scientific Sessions, Heart Rhythm, Presentation Abstract (2012).
Rhee, et al., "Presentation Abstract—Effects of suprathreshold vagal stimulation on stellate ganglion nerve activity in ambulatory dogs," 33rd Annual Scientific Sessions, Heart Rhythm (2012).
Riccio, et al., "Interganglionic segregation of distinct vagal afferent fibre phenotypes in guinea-pig airways," Journal of Physiology, 495.2, pp. 521-530 (1996).
Riddle, et al., "Epidemiologic Relationships Between A1C and All-Cause Mortality During a Median 3.4-Year Follow-up of Glycemic Treatment in the ACCORD Trial," Diabetes Care, vol. 33, No. 5, pp. 983-990 (May 2010).
Ridker, C-Reactive Protein: A Simple Test to Help Predict Risk of Heart Attack and Stroke, Journal of the American Heart Association, 108, pp. e81-e85 (2003).
Ridker, et al., "Comparison of C-Reactive Protein and Low-Density Lipoprotein Cholesterol Levels in the Prediction of First cardiovascular Events," New England Journal of Medicine, vol. 347, No. 20, pp. 1557-1566 (Nov. 14, 2002).
Ridker, et al., "C-Reactive Protein and Other Markers of Inflammation in the Prediction of Cardiovascular Disease in Women," The New England Journal of Medicine, vol. 342, No. 12, pp. 836-841 (Mar. 23, 2000).
Ridker, et al., "Inflammation, Pravastatin, and the Risk of Coronary Events After Myocardial Infarction in Patients With Average Cholesterol Levels," Circulation, Journal of the American Heart Association, 98, pp. 839-844 (1998).
Roger, et al., "Heart Disease and Stroke Statistics—2011 Update: A Report from the American Heart Association," Circulation, Journal of the American Heart Association. Available at http://circ.ahajournals.org/content/123/4/e18 (2010).
Romanovsky, et al., "The vagus nerve in the thermoregulatory response to systemic inflammation," Am. J. Physiol., 273, pp. R407-R413 (1997).
Rossi, et al., "Epicardial ganglionated plexus stimulation decreases postoperative inflammatory response in humans," Heart Rhythm, vol. 9, No. 6, pp. 943-950 (Jun. 2012).
Rouse, et al., "The haemodynamic actions of ZENCA ZD7288, a novel sino-atrial node function modulator, in the exercising beagle: a comparison with zategradine and propranolol," Abstract, British Journal of Pharmacology, 113(3):1071-7 (1994).

(56) References Cited

OTHER PUBLICATIONS

Rozman, et al., "Heart function influenced by selective mid-cervical left vagus nerve stimulation in a human case study," Hypertension Research, 32, pp. 1041-1043 (2009).
Rutecki, "Anatomical, Physiological and Theoretical Basis for the Antiepileptic Effect of Vagus Nerve Stimulation," Epilepsia, 31 (suppl. 2), pp. S1-S6 (1990).
Sabbah et al., "Vagus Nerve Stimulation in Experimental Heart Failure," Heart Failure Reviews, vol. 16, No. 2, Mar. 2011, pp. 171-178.
Sabbah, et al., "3722: Vagus nerve stimulation improves left ventricular function in heart failure: results of a 6 month investigation with a cross-over design in dogs with experimental heart failure," European Heart Journal, 32 (Abstract Supplement), pp. 642 (2011).
Sabbah, et al., "Baroreflex Activation Therapy for the Treatment of Heart Failure," Presentation available at http://www.cvrx.com/wp/wp-contenUuploads/2012/04/Dr.-Sabbah-Slides.pdf (2012).
Sabbah, et al., "Chronic Electrical Stimulation of the Carotid Sinus Baroreflex Improves Left Ventricular Function and Promotes Reversal of Ventricular Remodeling in Dogs with Advanced Heart Failure," Circulation Heart Failure, Journal of the American Heart Association, 4, pp. 65-70 (2011).
Sabbah, et al., "Vagus nerve stimulation in experimental heart failure," Heart Fail Rev, 16, pp. 171-178 (2011).
Samara, et al., "The Effects of Cardiac Resynchronization Therapy on Chronotropic Incompetence in Patients Intolerant of Beta Antagonist Therapy," Journal of Cardiac Failure, vol. 17, No. 8S, pp. S-54-S55 (Aug. 2011).
Sanner, et al., "P4743: Prediction of cardiovascular risk from nocturnal pulse wave signal using the autonomic state indicator (ASI) technology," European Heart Journal, 32 (Abstract Supplement), pp. 839 (2011).
Sato, et al., "Serial Circulating Concentrations of C-Reactive Protein, Interleukin (IL)-4, and IL-6 in Patients with Acute Left Heart Decompensation," Clin. Cardiol. 22, pp. 811-813 (1999).
Schauerte, "Time for Change: Cardiac neurophysiology meets cardiac electrophysiology," Editorial Commentary, Heart Rhythm Society (2013).
Schiereck, et al., "AV blocking due to asynchronous vagal stimulation in rats," Am J Physiol Heart Gire Physiol, 278, pp. H67-H73 (2000).
Schocken, et al., "Prevalence and Mortality Rate of Congestive Heart Failure in the United States," JACC, vol. 20, No. 2, pp. 301-306 (Aug. 1992).
Schwartz, "Vagal Stimulation for Heart Diseases: From Animals to Men," Circulation Journal, vol. 75, pp. 20-27 (Jan. 2011).
Schwartz, "Vagal stimulation for heart failure," Current Opinion in Cardiology, 26, pp. 51-54 (2011).
Schwartz, "Vagal stimulation for the treatment of heart failure: a translational success story," Heart, vol. 98, No. 23, pp. 1687-1690 (2012).
Schwartz, et al. Vagal stimulation for heart failure: Background and first in-man study, Heart Rhythm, 6, 11 suppl., pp. S76-S81 (Nov. 2009).
Schwartz, et al., "Autonomic mechanisms and sudden death. New insights from analysis of baroreceptor reflexes in conscious dogs with and without myocardial infarction," Circulation, Journal of the American Heart Association, 78, pp. 969-979 (1988).
Schwartz, et al., "Effects of Unilateral Cardiac Sympathetic Denervation on the Ventricular Fibrillation Threshold," The American Journal of Cardiology, vol. 37, pp. 1034-1040 (Jun. 1976).
Schwartz, et al., "Long term vagal stimulation in patients with advanced heart failure. First experience in man," European Journal of Heart Failure, 10, pp. 884-891 (2008).
Schwartz, et al., "Sympathetic-parasympathetic interaction in health and disease: abnormalities and relevance in heart failure," Heart Fail Rev, 16, pp. 101-107 (2011).
Seta, et al., "Basic Mechanisms in Heart Failure: The Cytokine Hypothesis," Journal of Cardiac Failure, vol. 2, No. 3, pp. 243-249 (1996).
Sha, et al., "Low-Level Right Vagal Stimulation: Anticholinergic and Antiadrenergic Effects," J Cardiovasc Electrophysiol, pp. 1-7 (Feb. 2011).
Shamoon, et al., The Diabetes Control and Complications Trial Research Group, "The effect of intensive treatment of diabetes on the development and progression of long-term complications in insulin-dependent diabetes mellitus," The New England Journal of Medicine, vol. 329, No. 14, pp. 977-986 (Sep. 30, 1993).
Shannon, "A Model of Safe Levels for Electrical Stimulation," IEEE Transactions on Biomedical Engineering, vol. 39, No. 4, pp. 424-426 (Apr. 1992).
Shen, et al., "Continuous Low-Level Vagus Nerve Stimulation Reduces Stellate Ganglion Nerve Activity and Paroxysmal Atrial Tachyarrhythmias in Ambulatory Canines," Circulation, Journal of the American Heart Association, 123, pp. 2204-2212 (2011).
Shen, etl al., "Low-level vagus nerve stimulation upregulates small conductance calcium-activated potassium channels in the stellate ganglion," Heart Rhythm, vol. 10, No. 6, pp. 910-915 (2013).
Shinohara, et al., "Heart Failure Decreases Nerve Activity in the Right Atrial Ganglionated Plexus," J Cardiovasc Electrophysiol, pp. 1-9 (2011).
Shioi, et al., "Increased Expression of Interleukin-1B and Monocyte Chemotactic and Activating Factor/Monocyte Chemoattractant Protein-1 in the Hypertrophied and Failing Heart with Pressure Overload," Gire Res., 81, pp. 664-671 (1997).
Singal, et al., "The role of oxidative stress in the genesis of heart disease," Cardiovascular Research, 40, pp. 426-432 (1998).
Spuck, et al., "Right-sided vagus nerve stimulation in humans: An effective therapy?" Epilepsy Research, pp. 1-3 (2008).
Stein, et al., "A Simple Method to Identify Sleep Apnea Using Holter Recordings," J Cardiovasc Electrophysiol, vol. 14, pp. 467-473 (May 2003).
Stein, et al., "Feasibility of Using Mobile Cardiac Outpatient Telemetry (MCOT) to Identify Severe Sleep Disorders" (2009).
Stieber, et al., "Bradycardic and proarrhythmic properties of sinus node inhibitors," Abstract, Molecular Pharmacology, 69(4):1328-37 (2006).
Taylor, et al., "The unequal influences of the left and right vagi on the control of the heart and pulmonary artery in the rattlesnake, Grata/us durissus," The Journal of Experimental Biology, 212, pp. 145-151 (2009).
Thayer, et al., "The role of vagal function in the risk for cardiovascular disease and mortality," Biological Psychology, 74, pp. 224-242 (2007).
Thollon, et al., "Electrophysiological effects of S 16257, a novel sino-atrial node modulator, on rabbit and guinea-pig cardiac preparations: comparison with UL-FS 49," Abstract, British Journal of Pharmacology, 112(1):37-42 (1994).
Tosato, et al., "Quasi-trapezoidal pulses to selectively block the activation of intrinsic laryngeal muscles during vagal nerve stimulation," J. Neural Eng., 4, pp. 205-212 (2007).
Tsutsumi, et al., "Modulation of the myocardial redox state by vagal nerve stimulation after experimental myocardial infarction," Cardiovascular Research, 77, pp. 713-721 (2008).
Tyler, et al., "Chapter 17—Electrodes for the Neural Interface," Neuromodulation, Academic Press (2009).
Ulphani, et al., "Quantitative analysis of parasympathetic innervation of the porcine heart," Heart Rhythm, 7, pp. 1113-1119 (2010).
Uthman, et al., "Effectiveness of vagus nerve stimulation in epilepsy patients. A 12-year observation," Neurology, 63, pp. 1124-1126 (2004).
Van Stee, "Autonomic Innervation of the Heart," Environmental Health Perspectives, vol. 26, pp. 151-158 (1978).
Vanoli, et al., "Vagal stimulation and prevention of sudden death in conscious dogs with a healed myocardial infarction," Circulation Research, Journal of the American Heart Association, 68, pp. 1471-1481 (1991).
Vasan, et al., "Inflammatory Markers and Risk of Heart Failure in Elderly Subjects Without Prior Myocardial Infarction," Circulation, Journal of the American Heart Association, 107, pp. 1486-1491 (2003).

(56) References Cited

OTHER PUBLICATIONS

Vassalle, et al., "An Analysis of Arrhythmias Induced by Ouabain in Intact Dogs," Circulation Research, Journal of the American Heart Association, 13, pp. 132-148 (1963).
Velagaleti, et al., "Long-Term Trends in the Incidence of heart Failure After Myocardial Infarction," 118, pp. 2057-2062 (2008).
Verrier, et al., "Microvolt T-Wave Alternans," Journal of the American College of Cardiology, vol. 58, No. 13, pp. 1309-1324 (2011).
Vimercati, et al., "Acute vagal stimulation attenuates cardiac metabolic response to B-adrenergic stress," The Journal of Physiology, vol. 500, No. 23, pp. 6065-6074 (2012).
Wang, et al., "Nicotinic acetylcholine receptor alpha-7 subunit is an essential regulator of inflammation," Nature, vol. 421, pp. 384-388 (Jan. 23, 2003).
Wang, et al., "Synaptic and Neurotransmitter Activation of Cardiac Vagal Neurons in the Nucleus Ambiguus," Annals New York Academy of Sciences, pp. 237-246 (2001).
Waninger, et al., "Characterization of Atrioventricular Nodal Response to Electrical Left Vagal Stimulation," Annals of Biomedical Engineering, vol. 27, pp. 758-762 (1999).
Wann, "Behavioural signs of depression and apoptosis in the limbic system following myocardial infarction: effects of sertraline," Journal of Psychopharmacology, 23(4), pp. 451-459 (2009).
Wann, et al., "Vulnerability for apoptosis in the limbic system after myocardial infarction in rats: a possible model for human postinfarct major depression," J Psychiatry Neurosci, 32(1):11-6, pp. 11-16 (2007).
Watkins, et al., "Cytokine-to-Brain Communication: A Review & Analysis of Alternative Mechanisms," Life Sciences, vol. 57, No. 11, pp. 1011-1026 (1995).
Whyte, et al., "Reactive oxygen species modulate neuronal excitability in rat intrinsic cardiac ganglia," Auton Neurosci, 150(1-2), pp. 45-52 (Oct. 5, 2009).
Wieland, et al., "Bradycardic and proarrhythmic properties of sinus node inhibitors," Abstract, Molecular Pharmacology, 69(4):1328-37 (2006).
Yang, et al., "Sustained increases in heart rate induced by time repetition of vagal stimulation in dogs," Am. J. Physiol., 249, pp. H703-H709 (1985).
Yin, et al., "Independent prognostic value of elevated high-sensitivity C-reactive protein in chronic heart failure," American Heart Journal, vol. 147, No. 5, pp. 931-938 (2004).
Yndestad, et al., "Systemic inflammation in heart failure—The whys and wherefores," Heart Fail Rev, 11, pp. 83-92 (2006).
Yoo, et al., "High-resolution measurement of electrically-evoked vagus nerve activity in the anesthetized dog," J. Neural Eng., 10, pp. 1-9 (2013).
Yoo, et al., "Selective Control of Physiological Responses by Temporally-Patterned Electrical Stimulation of the Canine Vagus Nerve," 33rd Annual International Conference of the IEEE EMBS (2011).
Yu, et al., "Interactions between atrial electrical remodeling and autonomic remodeling: How to break the vicious cycle," Heart Rhythm, 9, pp. 804-809 (2012).
Yu, et al., "Low-level transcutaneous electrical stimulation of the auricular branch of the vagus nerve: A noninvasive approach to treat the initial phase of atrial fibrillation," Heart Rhythm, 10, pp. 428-435 (2013).
Yuan, et al., "Gross and Microscopic Anatomy of the Canine Intrinsic Cardiac Nervous System," The Anatomical Record, 239, pp. 75-87 (1994).
Yusuf, et al., "Changes in Hypertension Treatment and in Congestive Heart Failure Mortality in the United States," Hypertension, Journal of the American Heart Association, 13:174-1179 (1989).
Zhang, et al., "Arrhythmias and vagus nerve stimulation," Heart Fail Rev, 16, pp. 147-161 (2011).
Zhang, et al., "Involvement of activated astrocyte and microglia of locus coeruleus in cardiac pain processing after acute cardiac injury," Neurol Res, 31, pp. 432-438 (2009).
Zhang, et al., "Relationship between right cervical vagus nerve stimulation and atrial fibrillation inducibility: Therapeutic intensities do not increase arrhythmogenesis," Heart Rhythm, 6, pp. 244-250 (2009).
Zhang, et al., "Therapeutic Effects of Selective Atrioventricular Node Vagal Stimulation in Atrial Fibrillation and Heart Failure," Journal of Cardiovascular Electrophysiology, vol. 24, Issue 1, pp. 86-91 (2012).
Zipes, et al., "Effects of selective vagal and stellate ganglion stimulation on atrial refractoriness," Cardiovascular Research, 8, pp. 647-655 (1974).
Zucker, et al., "Chronic Baroreceptor Activation Enhances Survival in Dogs with Pacing-Induced Heart Failure," Journal of the American Heart Association, Hypertension (2007).

* cited by examiner

Fig. 6 (con'd).
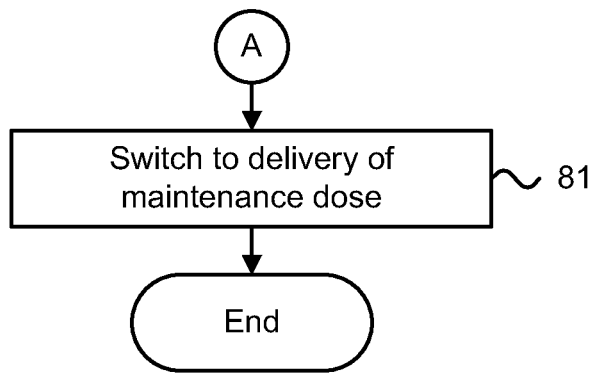
Fig. 7.
90
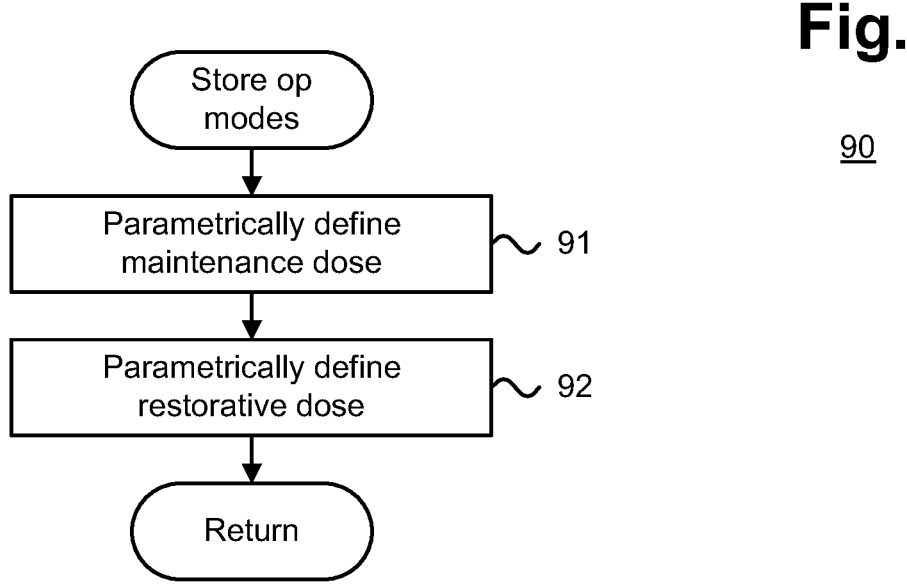

IMPLANTABLE NEUROSTIMULATOR-IMPLEMENTED METHOD FOR MANAGING TACHYARRHYTHMIA THROUGH VAGUS NERVE STIMULATION

CROSS-REFERENCE TO RELATED PATENT APPLICATIONS

This application is a continuation of U.S. patent Ser. No. 13/673,766, filed Nov. 9, 2012, which is hereby incorporated by reference in its entirety.

BACKGROUND

Congestive heart failure (CHF) and other forms of chronic cardiac dysfunction (CCD) are generally attributed to an autonomic imbalance of the sympathetic and parasympathetic nervous systems that, if left untreated, can lead to cardiac arrhythmogenesis, progressively worsening cardiac function and eventual patient death. CHF is pathologically characterized by an elevated neuroexcitatory state and is accompanied by physiological indications of impaired arterial and cardiopulmonary baroreflex function with reduced vagal activity.

CHF triggers compensatory activations of the sympathoadrenal (sympathetic) nervous system and the renin-angiotensin-aldosterone hormonal system, which initially help to compensate for deteriorating heart pumping function, yet, over time, can promote progressive left ventricular dysfunction and deleterious cardiac remodeling. Patients suffering from CHF are at increased risk of tachyarrhythmias, such as atrial fibrillation (AF), ventricular tachyarrhythmias (ventricular tachycardia (VT) and ventricular fibrillation (VF)), and atrial flutter, particularly when the underlying morbidity is a form of coronary artery disease, cardiomyopathy, mitral valve prolapse, or other valvular heart disease. Sympathoadrenal activation also significantly increases the risk and severity of tachyarrhythmias due to neuronal action of the sympathetic nerve fibers in, on, or around the heart and through the release of epinephrine (adrenaline), which can exacerbate an already-elevated heart rate.

VT originates solely in the lower heart in either the ventricular tissue or Purkinje fibers. During VT, electrical signals within the ventricles begin firing abnormally and cause a rapid rate of ventricular contraction; the rate is so rapid that the heart is unable to fill properly, thereby substantially reducing the forward flow, which results in dramatic reduction in the volume of blood ejected through the aortic valve into the peripheral vascular system. This sudden reduction in blood flow can have immediate deleterious consequences since the brain and other vital organ systems require adequate blood perfusion to maintain their biological integrity. When starved of blood, even for short periods of time, vital organ systems can be damaged. The brain is particularly sensitive to reduced cardiac output. Initially, during low flow conditions, such as during VT, the brain's electrical systems are affected, and patient consciousness may be compromised. If this low or no flow condition persists for minutes, brain tissue damage begins. After six to eight minutes, this damage can become permanent and may ultimately lead to chronic impairment or death, unless the hemodynamic compromise caused by the VT is immediately and definitively corrected. During the VT, action potentials circulating in the ventricles collide and interfere with the normal propagation of action potentials from the sinoatrial (SA) node and the resulting rapid heart rate causes the heart chambers to contract prematurely and without adequately filling, thus preventing proper blood flow and causing potentially lethal hemodynamic compromise.

While other forms of tachycardia, specifically supraventricular (SVT) and sinus tachycardia, are relatively benign unless episodic or prolonged, VT can present life-threatening risk and can degenerate into VF, asystole and sudden cardiac death. Both VT and particularly VF, as well as other forms of potentially life-threatening tachyarrhythmias, must be promptly treated to restore the heart to normal sinus rhythm. The current standard of care for treating VT includes, in order of increasing medical urgency, anti-arrhythmic medications, cardioversion, radiofrequency ablation, and heart surgery. Despite VT existing as an underlying complication of chronic cardiac dysfunction, the primary morbidity, CHF, is typically only managed through the prescription of pharmacological agents and application of dietary and lifestyle changes. As well, in contrast to the customary urgent treatment of VT, the medical measures for managing CHF are merely palliative, not curative. Patients often suffer side effects and other comorbidities, in addition to increased VT risk, due to disease progression.

The standard of care for managing CCD in general continues to evolve. For instance, new therapeutic approaches that employ electrical stimulation of neural structures that directly address the underlying cardiac autonomic nervous system imbalance and dysregulation have been proposed. In one form, controlled stimulation of the cervical vagus nerve beneficially modulates cardiovascular regulatory function. Currently, vagus nerve stimulation (VNS) is only approved for the clinical treatment of drug-refractory epilepsy and depression, although VNS has been proposed as a therapeutic treatment of CHF in general and has been demonstrated in canine studies as efficacious in simulated treatment of AF and heart failure, such as described in Zhang et al., "Therapeutic Effects of Selective Atrioventricular Node Vagal Stimulation in Atrial Fibrillation and Heart Failure," J. Cardiovasc. Electrophysiol., Vol. pp. 1-6 (Jul. 9, 2012), the disclosure of which is incorporated by reference.

Conventional general therapeutic alteration of cardiac vagal efferent activation through electrical stimulation targets only the efferent nerves of the parasympathetic nervous system, such as described in Sabbah et al., "Vagus Nerve Stimulation in Experimental Heart Failure," Heart Fail. Rev., 16:171-178 (2011), the disclosure of which is incorporated by reference. The Sabbah paper discusses canine studies using a vagus nerve stimulation system, manufactured by BioControl Medical Ltd., Yehud, Israel, which includes an electrical pulse generator, right ventricular endocardial sensing lead, and right vagus nerve cuff stimulation lead. The sensing lead enables stimulation of the right vagus nerve in a highly specific manner, which involves closed-loop synchronization of the vagus nerve stimulation pulse to the cardiac cycle. An asymmetric tri-polar nerve cuff electrode is implanted on the right vagus nerve at the mid-cervical position. The electrode provides cathodic induction of action potentials while simultaneously applying asymmetric anodal blocks that lead to preferential activation of vagal efferent fibers. Electrical stimulation of the right cervical vagus nerve is delivered only when heart rate increases beyond a preset threshold. Stimulation is provided at an impulse rate and intensity intended to reduce basal heart rate by ten percent by preferential stimulation of efferent vagus nerve fibers leading to the heart while blocking afferent neural impulses to the brain. Although effective in partially restoring baroreflex sensitivity and, in the canine model, increasing left ventricular ejection fraction and decreasing left ventricular end diastolic and end systolic volumes, the degree of therapeutic effect on parasympathetic activation occurs through incidental recruitment of afferent parasympathetic nerve fibers in the vagus, as well as through recruitment of efferent fibers. Efferent stimulation alone is less effective at restoring autonomic balance than bi-directional stimulation.

Other uses of electrical nerve stimulation for therapeutic treatment of various cardiac and physiological conditions are described. For instance, U.S. Pat. No. 6,600,954, issued Jul. 29, 2003 to Cohen et al. discloses a method and apparatus for selective control of nerve fiber activations. An electrode device is applied to a nerve bundle capable of generating, upon activation, unidirectional action potentials that propagate through both small diameter and large diameter sensory fibers in the nerve bundle, and away from the central nervous system. The device is particularly useful for reducing pain sensations in the legs and arms.

U.S. Pat. No. 6,684,105, issued Jan. 27, 2004 to Cohen et al. discloses an apparatus for treatment of disorders by unidirectional nerve stimulation. An apparatus for treating a specific condition includes a set of one or more electrode devices that are applied to selected sites of the central or peripheral nervous system of the patient. For some applications, a signal is applied to a nerve, such as the vagus nerve, to stimulate efferent fibers and treat motility disorders, or to a portion of the vagus nerve innervating the stomach to produce a sensation of satiety or hunger. For other applications, a signal is applied to the vagus nerve to modulate electrical activity in the brain and rouse a comatose patient, or to treat epilepsy and involuntary movement disorders.

U.S. Pat. No. 7,123,961, issued Oct. 17, 2006 to Kroll et al. discloses stimulation of autonomic nerves. An autonomic nerve is stimulated to affect cardiac function using a stimulation device in electrical communication with the heart by way of three leads suitable for delivering multi-chamber stimulation and shock therapy. For arrhythmia detection, the device utilizes atrial and ventricular sensing circuits to sense cardiac signals to determine whether a rhythm is physiologic or pathologic. The timing intervals between sensed events are classified by comparing them to a predefined rate zone limit and other characteristics to determine the type of remedial therapy needed, which includes bradycardia pacing, anti-tachycardia pacing, cardioversion shocks (synchronized with an R-wave), or defibrillation shocks (delivered asynchronously).

U.S. Pat. No. 7,225,017, issued May 29, 2007 to Shelchuk discloses terminating VT in connection with any stimulation device that is configured or configurable to stimulate nerves, or stimulate and shock a patient's heart. Parasympathetic stimulation is used to augment anti-tachycardia pacing, cardioversion, or defibrillation therapy. To sense atrial or ventricular cardiac signals and provide chamber pacing therapy, particularly on the left side of the patient's heart, the stimulation device is coupled to a lead designed for placement in the coronary sinus or its tributary veins. Cardioversion stimulation is delivered to a parasympathetic pathway upon detecting a ventricular tachycardia. A stimulation pulse is delivered via the lead to one or more electrodes positioned proximate to the parasympathetic pathway according to stimulation pulse parameters based on the probability of reinitiation of an arrhythmia.

U.S. Pat. No. 7,277,761, issued Oct. 2, 2007 to Shelchuk discloses vagal stimulation for improving cardiac function in heart failure patients. An autonomic nerve is stimulated to affect cardiac function using a stimulation device in electrical communication with the heart by way of three leads suitable for delivering multi-chamber endocardial stimulation and shock therapy. Where the stimulation device is intended to operate as an implantable cardioverter-defibrillator (ICD), the device detects the occurrence of an arrhythmia, and applies a therapy to the heart aimed at terminating the detected arrhythmia. Defibrillation shocks are generally of moderate to high energy level, delivered asynchronously, and pertaining exclusively to the treatment of fibrillation.

U.S. Pat. No. 7,295,881, issued Nov. 13, 2007 to Cohen et al. discloses nerve branch-specific action potential activation, inhibition and monitoring. Two preferably unidirectional electrode configurations flank a nerve junction from which a preselected nerve branch issues, proximally and distally to the junction, with respect to the brain. Selective nerve branch stimulation can be used with nerve-branch specific stimulation to achieve selective stimulation of a specific range of fiber diameters, restricted to a preselected nerve branch, including heart rate control, where activating only the vagal B nerve fibers in the heart, and not vagal A nerve fibers that innervate other muscles, can be desirous.

U.S. Pat. No. 7,778,703, issued Aug. 17, 2010 to Gross et al. discloses selective nerve fiber stimulation for treating heart conditions. An electrode device is adapted to be coupled to a vagus nerve of a subject and a control unit drives the electrode device by applying stimulating and inhibiting currents to the vagus nerve, which are capable of respectively inducing action potentials in a therapeutic direction in a first set and a second set of nerve fibers in the vagus nerve and inhibiting action potentials in the therapeutic direction in the second set of nerve fibers only. The nerve fibers in the second set have larger diameters than the nerve fibers in the first set. Typically, the system is configured to treat heart failure or heart arrhythmia, such as atrial fibrillation or tachycardia by slowing or stabilizing the heart rate, or reducing cardiac contractility.

U.S. Pat. No. 7,813,805, issued Oct. 12, 2010 to Farazi and U.S. Pat. No. 7,869,869, issued Jan. 11, 2011 to Farazi both disclose subcardiac threshold vagus nerve stimulation. A vagus nerve stimulator is configured to generate electrical pulses below a cardiac threshold, which are transmitted to a vagus nerve, so as to inhibit or reduce injury resulting from ischemia. For arrhythmia detection, a heart stimulator utilizes atrial and ventricular sensing circuits to sense cardiac signals to determine whether a rhythm is physiologic or pathologic. In low-energy cardioversion, an ICD device typically delivers a cardioversion stimulus synchronously with a QRS complex; thus, avoiding the vulnerable period of the T-wave and avoiding an increased risk of initiation of VF. In general, if anti-tachycardia pacing or cardioversion fails to terminate a tachycardia, then, for example, after a programmed time interval or if the tachycardia accelerates, the ICD device initiates defibrillation therapy.

Finally, U.S. Pat. No. 7,885,709, issued Feb. 8, 2011 to Ben-David discloses nerve stimulation for treating disorders. A control unit drives an electrode device to stimulate the vagus nerve, so as to modify heart rate variability, or to reduce heart rate, by suppressing the adrenergic (sympathetic) system. Typically, the system is configured to treat heart failure or heart arrhythmia, such as AF or tachycardia. In one embodiment, a control unit is configured to drive an electrode device to stimulate the vagus nerve, so as to modify heart rate variability to treat a condition of the subject. Therapeutic effects of reduction in heart rate variability include the narrowing of the heart rate range, thereby eliminating very slow heart rates and very fast heart rates. For this therapeutic application, the control unit is typically configured to reduce low-frequency heart rate variability, and to adjust the level of stimulation applied based on the circadian and activity cycles of the subject. Therapeutic effects also include maximizing the mechanical efficiency of the heart by maintaining relatively constant ventricular filling times and pressures. For example, this therapeutic effect may be beneficial for subjects suffering from atrial fibrillation, in which fluctuations in heart filling times and pressure reduce cardiac efficiency.

Accordingly, a need remains for an approach to therapeutically treating chronic cardiac dysfunction, including CHF, and cardiac arrhythmogenesis, specifically tachycardia, through a form of VNS to improve autonomic balance and cardiovascular regulatory function.

SUMMARY OF THE INVENTION

Excessive sustained activation of the sympathetic nervous system has a deleterious effect on long term cardiac performance and increases the risk of tachyarrhythmias, particularly in a patient with CCD. Bi-directional afferent and efferent neural stimulation through the vagus nerve can beneficially restore autonomic balance and improve long term clinical outcome. The neural stimulation is provided in a low level maintenance dose independent of cardiac cycle. VNS delivery can be provided through an implantable vagus neurostimulator and electrode lead, which begins delivering a restorative dose at a higher level of intensity than the maintenance dose upon sensing a condition indicative of spontaneous tachyarrhythmia. VNS maintenance dose delivery is only continually resumed if, during post-suspension monitoring, tachyarrhythmia is not found to recur.

One embodiment provides an implantable neurostimulator-implemented method for managing tachyarrhythmias through vagus nerve stimulation. An implantable neurostimulator, including a pulse generator, is configured to deliver electrical therapeutic stimulation in a manner that results in creation and propagation (in both afferent and efferent directions) of action potentials within neuronal fibers comprising the cervical vagus nerve of a patient. Operating modes are stored in the pulse generator. A maintenance dose of the electrical therapeutic stimulation is parametrically defined and tuned to restore cardiac autonomic balance through continuously-cycling, intermittent and periodic electrical pulses. A restorative dose of the electrical therapeutic stimulation is parametrically defined and tuned to prevent initiation of or disrupt tachyarrhythmia through periodic electrical pulses delivered at higher intensity, which could be higher output current, higher duty cycle, higher frequency, or longer pulse width, than the maintenance dose. The maintenance dose is therapeutically delivered to the vagus nerve independent of cardiac cycle via a pulse generator included in the implantable eurostimulator through at least a pair of helical electrodes electrically coupled to the pulse generator via a nerve stimulation therapy lead. The patient's normative physiology is monitored via a physiological sensor included in the implantable neurostimulator, and upon sensing a condition indicative of tachyarrhythmia, is switched to delivering the restorative dose to the vagus nerve via the pulse generator through the pair of helical electrodes.

A further embodiment provides an implantable neurostimulator-implemented method for managing tachyarrhythmias through vagus nerve stimulation. A maintenance dose of electrical therapeutic stimulation for delivery via an implantable neurostimulator is defined and tuned to restore cardiac autonomic balance through continuously-cycling, intermittent and periodic electrical pulses. A restorative dose of electrical therapeutic stimulation for delivery via the implantable neurostimulator is defined and tuned to prevent initiation of or disrupt tachyarrhythmia through periodic electrical pulses delivered at higher intensity, which could be higher output current, higher duty cycle, higher frequency, or longer pulse width, than the maintenance dose. Vagus nerve stimulation therapy is provided to the vagus nerve through at least a pair of helical electrodes via a stimulation therapy lead electrically coupled to a pulse generator included in the implantable neurostimulator. The maintenance dose is therapeutically delivered via the pulse generator to the vagus nerve independent of cardiac cycle in a manner that results in creation and propagation (in both afferent and efferent directions) of action potentials within neuronal fibers comprising a cervical vagus nerve of a patient. The patient's physiology is periodically monitored via a physiological sensor included in the implantable neurostimulator. Upon sensing a condition indicative of tachyarrhythmia, therapy delivery is switched to delivering the restorative dose to the vagus nerve. Upon sensing a condition indicative of a recurrence of the tachyarrhythmia, the therapeutic delivery of the restorative dose to the vagus nerve is continued via the pulse generator.

By improving autonomic balance and cardiovascular regulatory function, therapeutic VNS operates acutely to decrease heart rate, reflexively increase heart rate variability and coronary flow, reduce cardiac workload through vasodilation, and improve left ventricular relaxation without aggravating comorbid tachyarrhythmia or other cardiac arrhythmic conditions. Over the long term, low dosage VNS provides the chronic benefits of decreased negative cytokine production, increased baroreflex sensitivity, increased respiratory gas exchange efficiency, favorable gene expression, renin-angiotensin-aldosterone system down-regulation, and anti-arrhythmic, anti-apoptotic, and ectopy-reducing anti-inflammatory effects.

Still other embodiments of the present invention will become readily apparent to those skilled in the art from the following detailed description, wherein are described embodiments by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIG. 7 is a flow diagram showing a routine for storing operating modes for use with the method of FIG. 6.

DETAILED DESCRIPTION

Changes in autonomic control of the cardiovascular systems of patients suffering from CHF and other cardiovascular diseases push the autonomic nervous system out of balance and favor increased sympathetic and decreased parasympathetic central outflow. The imbalance is accompanied by pronounced elevation of basal heart rate arising from chronic sympathetic hyperactivation along the neurocardiac axis.

Peripheral neurostimulation therapies that target the imbalance of the autonomic nervous system have been shown to improve clinical outcomes in patients treated for three to twelve months. Specifically, bi-directional autonomic regulation therapy results in simultaneous creation and propagation of efferent and afferent action potentials within afferent and efferent nerve fibers comprising the vagus nerve. The therapy directly restores autonomic balance by engaging both medullary and cardiovascular reflex control components of the autonomic nervous system. Upon stimulation of the cervical vagus nerve, action potentials propagate away from the stimulation site in two directions, efferently toward the heart and afferently toward the brain. Efferent action potentials influence the intrinsic cardiac nervous system and the heart, while afferent action potentials influence central elements of the nervous system.

Figure 1:
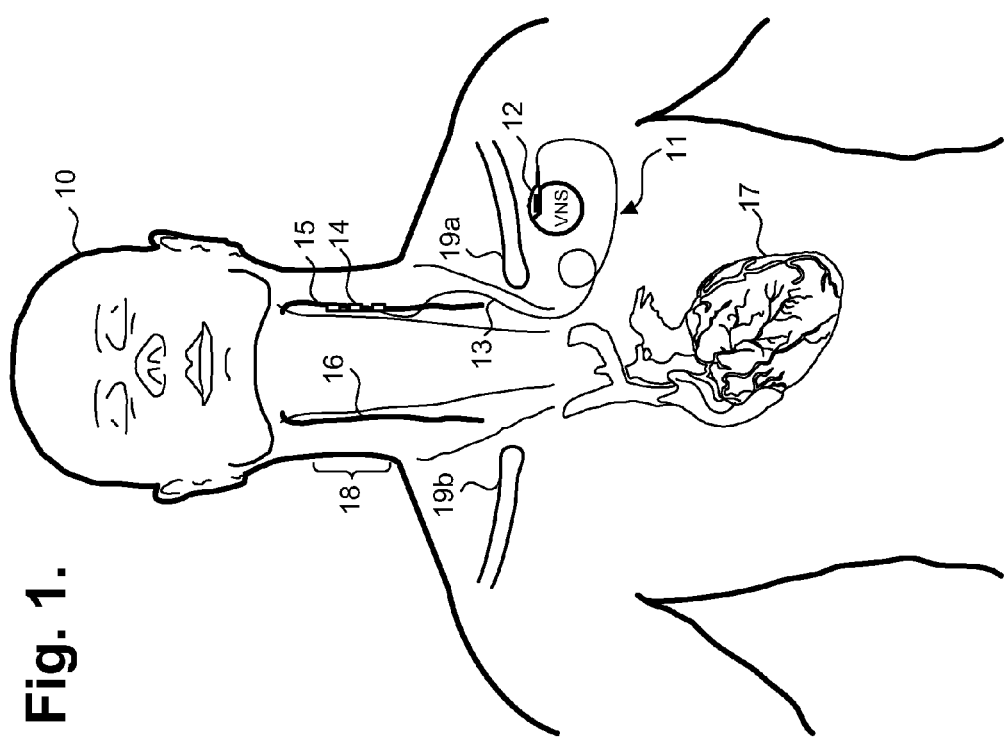
FIG. 1 is a front anatomical diagram showing, by way of example, placement of an implantable vagus stimulation device in a male patient, in accordance with one embodiment.

An implantable vagus nerve stimulator with integrated heart rate sensor, such as used to treat drug-refractory epilepsy and depression, can be adapted for use in managing chronic cardiac dysfunction through therapeutic bi-directional vagal stimulation. In addition, an integrated heart rate sensor can provide continual leadless heart rate monitoring that can be used in detecting arrhythmia, particularly VT, and confirming therapeutic efficacy. FIG. 1 is a front anatomical diagram showing, by way of example, placement of an implantable vagus nerve stimulation (VNS) device 11 in a male patient 10, in accordance with one embodiment. The VNS provided through the stimulation device 11 operates under several mechanisms of action. These mechanisms include increasing parasympathetic outflow and inhibiting sympathetic effects by blocking norepinephrine release. More importantly, VNS triggers the release of acetylcholine (ACh) into the synaptic cleft, which has beneficial anti-arrhythmic, anti-apoptotic, and ectopy-reducing anti-inflammatory effects.

The implantable vagus stimulation device 11 includes at least three implanted components, an implantable neurostimulator 12, a therapy lead 13, and helical electrodes 14. The implantable vagus stimulation device 11 can be remotely accessed following implant through an external programmer by which the neurostimulator 12 can be remotely checked and programmed by healthcare professionals; an external magnet, such as described in commonly-assigned U.S. patent application, entitled "Implantable Device For Facilitating Control Of Electrical Stimulation Of Cervical Vagus Nerves For Treatment Of Chronic Cardiac Dysfunction," Ser. No. 13/314,130, filed on Dec. 7, 2011, now U.S. Pat. No. 8,600,505, issued Dec. 3, 2013, the disclosure of which is incorporated by reference, for basic patient control; and an electromagnetic controller, such as described in commonly-assigned U.S. patent application, entitled "Vagus Nerve Neurostimulator With Multiple Patient-Selectable Modes For Treating Chronic Cardiac Dysfunction," Ser. No. 13/352,244, filed on Jan. 17, 2012, now U.S. Pat. No. 8,571,654, issued Oct. 29, 2013, the disclosure of which is incorporated by reference, that enables the patient 10 to exercise increased control over therapy delivery and suspension. Together, the implantable vagus stimulation device 11 and one or more of the external components form a VNS therapeutic delivery system.

The neurostimulator 12 is implanted in the patient's right or left pectoral region generally on the same side (ipsilateral) as the vagus nerve 15, 16 to be stimulated, although other neurostimulator-vagus nerve configurations, including contra-lateral and bi-lateral are possible. The helical electrodes 14 are generally implanted on the vagus nerve 15, 16 about halfway between the clavicle 19*a-b* and the mastoid process. The therapy lead 13 and helical electrodes 14 are implanted by first exposing the carotid sheath and chosen vagus nerve 15, 16 through a latero-cervical incision on the ipsilateral side of the patient's neck 18. The helical electrodes 14 are then placed onto the exposed nerve sheath and tethered. A subcutaneous tunnel is formed between the respective implantation sites of the neurostimulator 12 and helical electrodes 14, through which the therapy lead 13 is guided to the neurostimulator 12 and securely connected.

In one embodiment, the neural stimulation is provided in a low level maintenance dose independent of cardiac cycle and, upon sensing a condition indicative of spontaneous tachyarrhythmia, the stimulation device 11 delivers a restorative dose of VNS at a higher level of intensity than the maintenance dose. VNS maintenance dose delivery is only continually resumed if, during post-suspension monitoring, tachyarrhythmia is not found to recur. The stimulation device 11 bi-directionally stimulates the vagus nerve 15, 16 through multimodal application of continuously-cycling, intermittent and periodic electrical stimuli, which are parametrically defined through stored stimulation parameters and timing cycles, as further described infra with reference to FIG. 7. In a further embodiment, bradycardia in VNS-titrated patients can be managed through suspension of on-going low-level VNS, such as described in commonly-assigned U.S. patent application, entitled "Implantable Neurostimulator-Implemented Method for Managing Bradycardia through Vagus Nerve Stimulation," Ser. No. 13/554,656, filed on Jul. 20, 2012, pending, the disclosure of which is incorporated by reference. In a still further embodiment, prolonged activation of the sympathetic nervous system during post-exercise recovery periods, particularly in patients with CCD, can be managed through application of an enhanced dose of VNS, such as described in commonly-assigned U.S. patent application, entitled "Implantable Neurostimulator-Implemented Method for Enhancing Post-Exercise Recovery through Vagus Nerve Stimulation," Ser. No. 13/673,795, filed on Nov. 9, 2012 pending, the disclosure of which is incorporated by reference.

Both sympathetic and parasympathetic nerve fibers are stimulated. Cervical vagus nerve stimulation results in propagation of action potentials from the site of stimulation in a manner that results in creation and propagation (in both afferent and efferent directions) of action potentials within neuronal fibers comprising the cervical vagus nerve to restore cardiac autonomic balance. Afferent action potentials propagate toward the parasympathetic nervous system's origin in the medulla in the nucleus ambiguus, nucleus tractus solitarius, and the dorsal motor nucleus, as well as toward the sympathetic nervous system's origin in the intermediolateral cell column of the spinal cord. Efferent action potentials propagate toward the heart 17 to activate the components of the heart's intrinsic nervous system. Either the left or right vagus nerve 15, 16 can be stimulated by the stimulation device 11. The right vagus nerve 16 has a moderately lower stimulation threshold than the left vagus nerve 15 for heart rate affects at the same parametric levels.

Figure 2A:
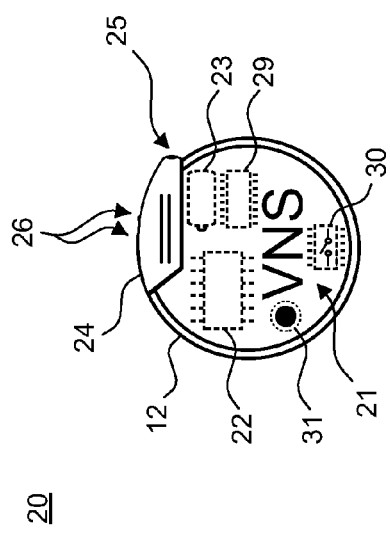
FIGS. 2A and 2B are diagrams respectively showing the implantable neurostimulator and the simulation therapy lead of FIG. 1.
Figure 2B:
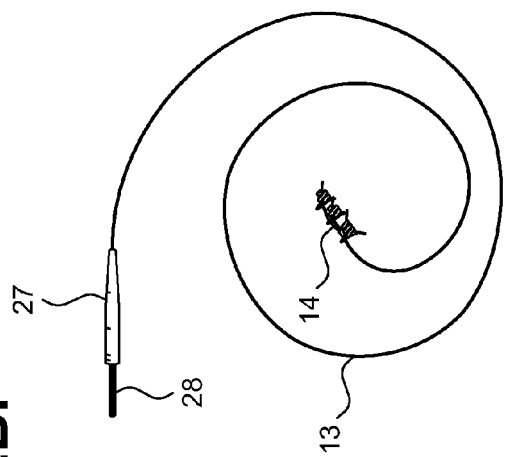

The VNS therapy is delivered autonomously to the patient's vagus nerve 15, 16 through three implanted components that include a neurostimulator 12, therapy lead 13, and helical electrodes 14. FIGS. 2A and 2B are diagrams respectively showing the implantable neurostimulator 12 and the simulation therapy lead 13 of FIG. 1. In one embodiment, the neurostimulator 12 can be adapted from a VNS Therapy AspireSR Model 106 pulse generator, manufactured and sold by Cyberonics, Inc., Houston, Tex., although other manufactures and types of single-pin receptacle implantable VNS neurostimulators with integrated leadless heart rate sensors could also be used. The stimulation therapy lead 13 and helical electrodes 14 are generally fabricated as a combined assembly and can be adapted from a Model 302 lead, PerenniaDURA Model 303 lead, or PerenniaFLEX Model 304 lead, also manufactured and sold by Cyberonics, Inc., in two sizes based on helical electrode inner diameter, although other manufactures and types of single-pin receptacle-compatible therapy leads and electrodes could also be used.

Referring first to FIG. 2A, the neurostimulator 12 provides multimodal vagal stimulation. In a maintenance mode, continuously-cycling, intermittent and periodic ON-OFF cycles of VNS are delivered that produce action potentials in the underlying nerves that propagate bi-directionally. In a restorative mode, VNS tuned to prevent initiation of or disrupt tachyarrhythmia through continuously-cycling, intermittent and periodic ON-OFF cycles of VNS delivered at higher intensity, which could be higher output current, higher duty cycle, higher frequency, longer pulse width, or a combination of the foregoing parameters, than the maintenance dose are delivered in response to the onset or progression of tachyarrhythmias.

The neurostimulator 12 includes an electrical pulse generator that is tuned to restore autonomic balance by triggering action potentials that propagate both afferently and efferently within the vagus nerve 15, 16. The neurostimulator 12 is enclosed in a hermetically sealed housing 21 constructed of a biocompatible, implantation-safe material, such as titanium. The housing 21 contains electronic circuitry 22 powered by a primary battery 23, such as a lithium carbon monoflouride battery. The electronic circuitry 22 is implemented using complementary metal oxide semiconductor integrated circuits that include a microprocessor controller that executes a control program according to stored stimulation parameters and timing cycles; a voltage regulator that regulates system power; logic and control circuitry, including a recordable memory 29 within which the stimulation parameters are stored, that controls overall pulse generator function, receives and implements programming commands from the external programmer, or other external source, collects and stores telemetry information, processes sensory input, and controls scheduled and sensory-based therapy outputs; a transceiver that remotely communicates with the external programmer using radio frequency signals; an antenna, which receives programming instructions and transmits the telemetry information to the external programmer; and a reed switch 30 that provides remote access to the operation of the neurostimulator 12 using an external programmer, a simple patient magnet, or an electromagnetic controller. The recordable memory 29 can include both volatile (dynamic) and persistent (static) forms of memory, such as firmware within which the stimulation parameters and timing cycles can be stored. Other electronic circuitry and components are possible.

Externally, the neurostimulator 12 includes a header 24 to securely receive and connect to the therapy lead 13. In one embodiment, the header 24 encloses a receptacle 25 into which a single pin for the therapy lead 13 can be received, although two or more receptacles could also be provided, along with the requisite additional electronic circuitry 22. The header 24 internally includes a lead connector block (not shown) and a set of set screws 26.

The housing 21 also contains a heart rate sensor 31 that is electrically interfaced with the logic and control circuitry, which receives the patient's sensed heart rate as sensory inputs. The heart rate sensor 31 monitors heart rate using an ECG-type electrode. Through the electrode, the patient's heart beat can be sensed by detecting ventricular depolarization. In a further embodiment, a plurality of electrodes can be used to sense voltage differentials between electrode pairs, which can undergo signal processing for cardiac physiological measures, for instance, detection of the P-wave, QRS complex, and T-wave. The heart rate sensor 31 provides the sensed heart rate to the control and logic circuitry as sensory inputs that can be used to determine the onset or presence of arrhythmias, particularly VT, as further described infra with reference to FIG. 8.

The neurostimulator 12 is preferably interrogated prior to implantation and throughout the therapeutic period with a healthcare provider-operable external programmer and programming wand (not shown) for checking proper operation, downloading recorded data, diagnosing problems, and programming operational parameters. Generally, use of the external programmer is restricted to healthcare providers, while more limited manual control is provided to the patient through "magnet mode." In one embodiment, the external programmer executes application software specially designed to interrogate the neurostimulator 12. The programming computer interfaces to the programming wand through a standardized wired or wireless data connection. The programming wand can be adapted from a Model 201 Programming Wand, manufactured and sold by Cyberonics, Inc. and the application software can be adapted from the Model 250 Programming Software suite, licensed by Cyberonics, Inc. Other configurations and combinations of external programmer, programming wand and application software are possible.

The neurostimulator 12 delivers VNS under control of the electronic circuitry 22. The stored stimulation parameters are programmable. Each stimulation parameter can be independently programmed to define the characteristics of the cycles of therapeutic stimulation and inhibition to ensure optimal stimulation for a patient 10. The programmable stimulation parameters include output current, signal frequency, pulse width, signal ON time, signal OFF time, magnet activation (for VNS specifically triggered by "magnet mode"), and reset parameters. Other programmable parameters are possible. In addition, sets or "profiles" of pre-selected stimulation parameters can be provided to physicians with the external programmer and fine-tuned to a patient's physiological requirements prior to being programmed into the neurostimulator 12, such as described in commonly-assigned U.S. patent application, entitled "Computer-Implemented System and Method for Selecting Therapy Profiles of Electrical Stimulation of Cervical Vagus Nerves for Treatment of Chronic Cardiac Dysfunction," Ser. No. 13/314,138, filed on Dec. 7, 2011, now U.S. Pat. No. 8,630,709, the disclosure of which is incorporated by reference.

Referring next to FIG. 2B, the therapy lead 13 delivers an electrical signal from the neurostimulator 12 to the vagus nerve 15, 16 via the helical electrodes 14. On a proximal end, the therapy lead 13 has a lead connector 27 that transitions an insulated electrical lead body to a metal connector pin 28. During implantation, the connector pin 28 is guided through the receptacle 25 into the header 24 and securely fastened in place using the set screws 26 to electrically couple the therapy lead 13 to the neurostimulator 12. On a distal end, the therapy lead 13 terminates with the helical electrode 14, which bifurcates into a pair of anodic and cathodic electrodes 62 (as further described infra with reference to FIG. 4). In one embodiment, the lead connector 27 is manufactured using silicone and the connector pin 28 is made of stainless steel, although other suitable materials could be used, as well. The insulated lead body 13 utilizes a silicone-insulated alloy conductor material.

Preferably, the helical electrodes 14 are placed over the cervical vagus nerve 15, 16 at the location below where the superior and inferior cardiac branches separate from the cervical vagus nerve. In alternative embodiments, the helical electrodes may be placed at a location above where one or both of the superior and inferior cardiac branches separate from the cervical vagus nerve. In one embodiment, the helical electrodes 14 are positioned around the patient's vagus nerve oriented with the end of the helical electrodes 14 facing the patient's head. In an alternate embodiment, the helical electrodes 14 are positioned around the patient's vagus nerve 15, 16 oriented with the end of the helical electrodes 14 facing the patient's heart 17. At the distal end, the insulated electrical lead body 13 is bifurcated into a pair of lead bodies that are connected to a pair of electrodes proper. The polarity of the electrodes could be configured into a monopolar cathode, a proximal anode and a distal cathode, or a proximal cathode and a distal anode.

Therapeutically, the VNS is delivered as a multimodal set of therapeutic and event-based doses, which are system output behaviors that are pre-specified within the neurostimulator 12 through the stored stimulation parameters and timing cycles implemented in firmware and executed by the microprocessor controller. The therapeutic doses include a cardiac cycle-independent maintenance dose that includes continuously-cycling, intermittent and periodic cycles of electrical stimulation during periods in which the pulse amplitude is greater than 0 mA ("therapy ON") and during periods in which the pulse amplitude is 0 mA ("therapy OFF"). The therapeutic doses also include a restorative dose at a higher level of intensity than the maintenance dose, which could be higher output current, higher duty cycle, higher frequency, longer pulse width, or a combination of the foregoing parameters, in response to the presence of tachyarrhythmias.

The neurostimulator 12 can operate either with or without an integrated heart rate sensor (provided that patient physiology can be monitored through some other type of sensing mechanism), such as respectively described in commonly-assigned U.S. patent application, entitled "Implantable Device for Providing Electrical Stimulation of Cervical Vagus Nerves for Treatment of Chronic Cardiac Dysfunction with Leadless Heart Rate Monitoring," Ser. No. 13/314,126, filed on Dec. 7, 2011, pending, and U.S. patent application, entitled "Implantable Device for Providing Electrical Stimulation of Cervical Vagus Nerves for Treatment of Chronic Cardiac Dysfunction," Ser. No. 13/314,119, filed on Dec. 7, 2011, pending, the disclosures of which are hereby incorporated by reference herein in their entirety. Additionally, where an integrated leadless heart rate monitor is available, the neurostimulator 12 can provide autonomic cardiovascular drive evaluation and self-controlled titration, such as respectively described in commonly-assigned U.S. patent application, entitled "Implantable Device for Evaluating Autonomic Cardiovascular Drive in a Patient Suffering from Chronic Cardiac Dysfunction," Ser. No. 13/314,133, filed on Dec. 7, 2011, pending, and U.S. patent application, entitled "Implantable Device for Providing Electrical Stimulation of Cervical Vagus Nerves for Treatment of Chronic Cardiac Dysfunction with Bounded Titration," Ser. No. 13/314,135, filed on Dec. 7, 2011, now U.S. Pat. No. 8,577,458, issued Nov. 5, 2013, the disclosures of which are incorporated by reference. Finally, the neurostimulator 12 can be used to counter natural circadian sympathetic surge upon awakening and manage the risk of cardiac arrhythmias during or attendant to sleep, particularly sleep apneic episodes, such as respectively described in commonly-assigned U.S. patent application, entitled "Implantable Neurostimulator-Implemented Method For Enhancing Heart Failure Patient Awakening Through Vagus Nerve Stimulation," Ser. No. 13/673,811, filed on Nov. 9, 2012, now U.S. Pat. No. 8,923,964, issued Dec. 30, 2014, the disclosure of which is incorporated by reference.

Figure 3:
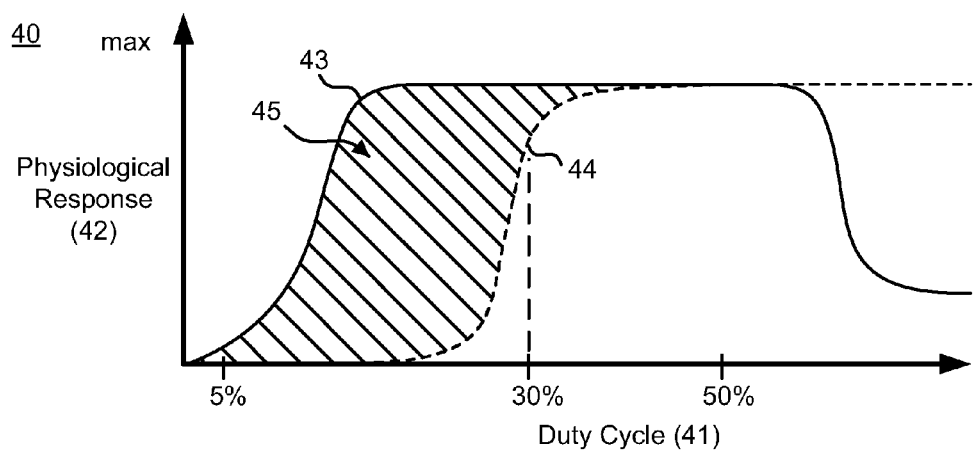
FIG. 3 is a graph showing, by way of example, the relationship between the targeted therapeutic efficacy and the extent of potential side effects resulting from use of the implantable neurostimulator of FIG. 1.

Therapeutically, VNS is delivered as a heart failure therapy independent of cardiac cycle and in a maintenance dose having an intensity that is insufficient to elicit side-effects, such as cardiac arrhythmias. The VNS can be delivered with a periodic duty cycle in the range of 2% to 89% with a preferred range of around 4% to 36% that is delivered as a low intensity maintenance dose. The selection of duty cycle is a tradeoff among competing medical considerations. FIG. 3 is a graph 40 showing, by way of example, the relationship between the targeted therapeutic efficacy 43 and the extent of potential side effects 44 resulting from use of the implantable neurostimulator 12 of FIG. 1. The x-axis represents the duty cycle 41. The duty cycle is determined by dividing the stimulation ON time by the sum of the ON and OFF times of the neurostimulator 12 during a single ON-OFF cycle. However, the stimulation time may also need to include ramp-up time and ramp-down time, where the stimulation frequency exceeds a minimum threshold (as further described infra with reference to FIG. 5). The y-axis represents physiological response 42 to VNS therapy. The physiological response 42 can be expressed quantitatively for a given duty cycle 41 as a function of the targeted therapeutic efficacy 43 and the extent of potential side effects 44, as described infra. The maximum level of physiological response 42 ("max") signifies the highest point of targeted therapeutic efficacy 43 or potential side effects 44.

Targeted therapeutic efficacy 43 and the extent of potential side effects 44 can be expressed as functions of duty cycle 41 and physiological response 42. The targeted therapeutic efficacy 43 represents the intended effectiveness of VNS in provoking a beneficial physiological response for a given duty cycle and can be quantified by assigning values to the various acute and chronic factors that contribute to the physiological response 42 of the patient 10 due to the delivery of therapeutic VNS. Acute factors that contribute to the targeted therapeutic efficacy 43 include beneficial changes in heart rate variability and increased coronary flow, reduction in cardiac workload through vasodilation, and improvement in left ventricular relaxation. Chronic factors that contribute to the targeted therapeutic efficacy 43 include improved cardiovascular regulatory function, as well as decreased negative cytokine production, increased baroreflex sensitivity, increased respiratory gas exchange efficiency, favorable gene expression, renin-angiotensin-aldosterone system down-regulation, anti-arrhythmic, anti-apoptotic, and ectopy-reducing anti-inflammatory effects. These contributing factors can be combined in any manner to express the relative level of targeted therapeutic efficacy 43, including weighting particular effects more heavily than others or applying statistical or numeric functions based directly on or derived from observed physiological changes. Empirically, targeted therapeutic efficacy 43 steeply increases beginning at around a 5% duty cycle, and levels off in a plateau near the maximum level of physiological response at around a 30% duty cycle. Thereafter, targeted therapeutic efficacy 43 begins decreasing at around a 50% duty cycle and continues in a plateau near a 25% physiological response through the maximum 100% duty cycle.

Figure 4:
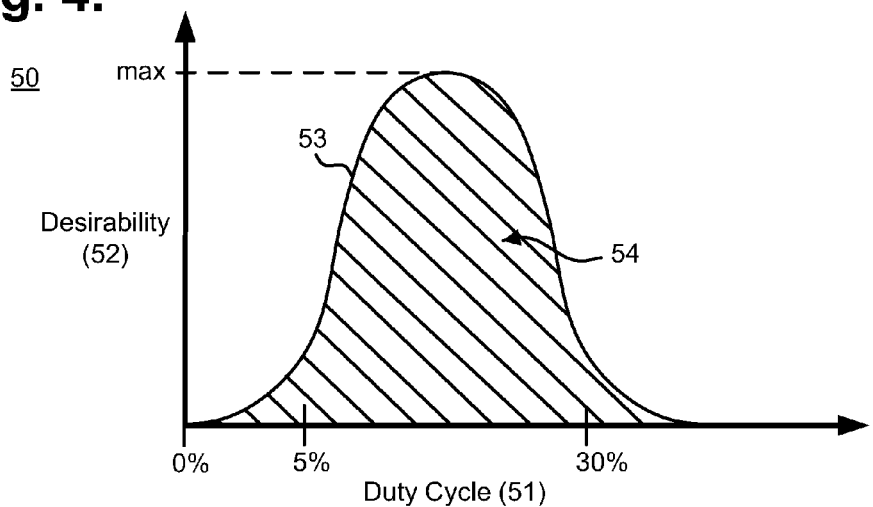
FIG. 4 is a graph showing, by way of example, the optimal duty cycle range based on the intersection depicted in FIG. 3.

The intersection 45 of the targeted therapeutic efficacy 43 and the extent of potential side effects 44 represents one optimal duty cycle range for VNS. FIG. 4 is a graph 50 showing, by way of example, the optimal duty cycle range 53 based on the intersection 45 depicted in FIG. 3. The x-axis represents the duty cycle 51 as a percentage of stimulation time over inhibition time. The y-axis represents therapeutic points 52 reached in operating the neurostimulator 12 at a given duty cycle 51. The optimal duty range 53 is a function 54 of the intersection 44 of the targeted therapeutic efficacy 43 and the extent of potential side effects 44. The therapeutic operating points 52 can be expressed quantitatively for a given duty cycle 51 as a function of the values of the targeted therapeutic efficacy 43 and the extent of potential side effects 44 at their point of intersection in the graph 40 of FIG. 3. The optimal therapeutic operating point 55 ("max") signifies a tradeoff that occurs at the point of highest targeted therapeutic efficacy 43 in light of lowest potential side effects 44 and that point will typically be found within the range of a 5% to 30% duty cycle 51. Other expressions of duty cycles and related factors are possible.

Figure 5:
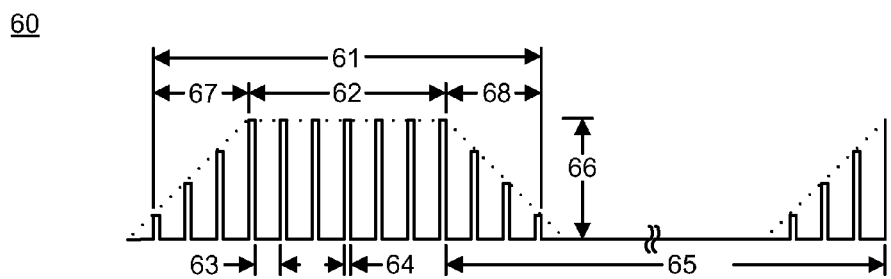
FIG. 5 is a timing diagram showing, by way of example, a stimulation cycle and an inhibition cycle of VNS as provided by implantable neurostimulator of FIG. 1.

Therapeutically and in the absence of patient physiology of possible medical concern, such as cardiac arrhythmias, VNS is delivered in a low level maintenance dose that uses alternating cycles of stimuli application (ON) and stimuli inhibition (OFF) that are tuned to activate both afferent and efferent pathways. Stimulation results in parasympathetic activation and sympathetic inhibition, both through centrally-mediated pathways and through efferent activation of preganglionic neurons and local circuit neurons. FIG. 5 is a timing diagram showing, by way of example, a stimulation cycle and an inhibition cycle of VNS 60 as provided by implantable neurostimulator 12 of FIG. 1. The stimulation parameters enable the electrical stimulation pulse output by the neurostimulator 12 to be varied by both amplitude (output current 66) and duration (pulse width 64). The number of output pulses delivered per second determines the signal frequency 63. In one embodiment, a pulse width in the range of 100 to 250 µsec delivers between 0.02 and 50 mA of output current at a signal frequency of about 20 Hz, although other therapeutic values could be used as appropriate.

In the simplest case, the stimulation time is the time period during which the neurostimulator 12 is ON and delivering pulses of stimulation. The OFF time 65 is always the time period occurring in-between stimulation times 61 during which the neurostimulator 12 is OFF and inhibited from delivering stimulation. In one embodiment, the neurostimulator 12 implements a ramp-up time 67 and a ramp-down time 68 that respectively precede and follow the ON time 62 during which the neurostimulator 12 is ON and delivering pulses of stimulation at the full output current 66. The ramp-up time 67 and ramp-down time 68 are used when the stimulation frequency is at least 10 Hz, although other minimum thresholds could be used, and both ramp-up and ramp-down times 67, 68 last two seconds, although other time periods could also be used. The ramp-up time 67 and ramp-down time 68 allow the strength of the output current 66 of each output pulse to be gradually increased and decreased, thereby avoiding deleterious reflex behavior due to sudden delivery or inhibition of stimulation at a programmed intensity.

The triggering of CHF compensatory mechanisms underlying a chronic cardiac dysfunction increases the risk of tachyarrhythmias. Although delivered in a maintenance dose having an intensity that is insufficient to elicit side-effects, such as cardiac arrhythmias, therapeutic VNS can nevertheless potentially ameliorate pathological tachyarrhythmias in some patients. Although VNS has been shown to decrease defibrillation threshold, VNS will not terminate VF in the absence of defibrillation. VNS prolongs ventricular action potential duration, so may be effective in terminating VT. In addition, the effect of VNS on the AV node may be beneficial in patients with AF by slowing conduction to the ventricles and controlling ventricular rate.

Figure 6:
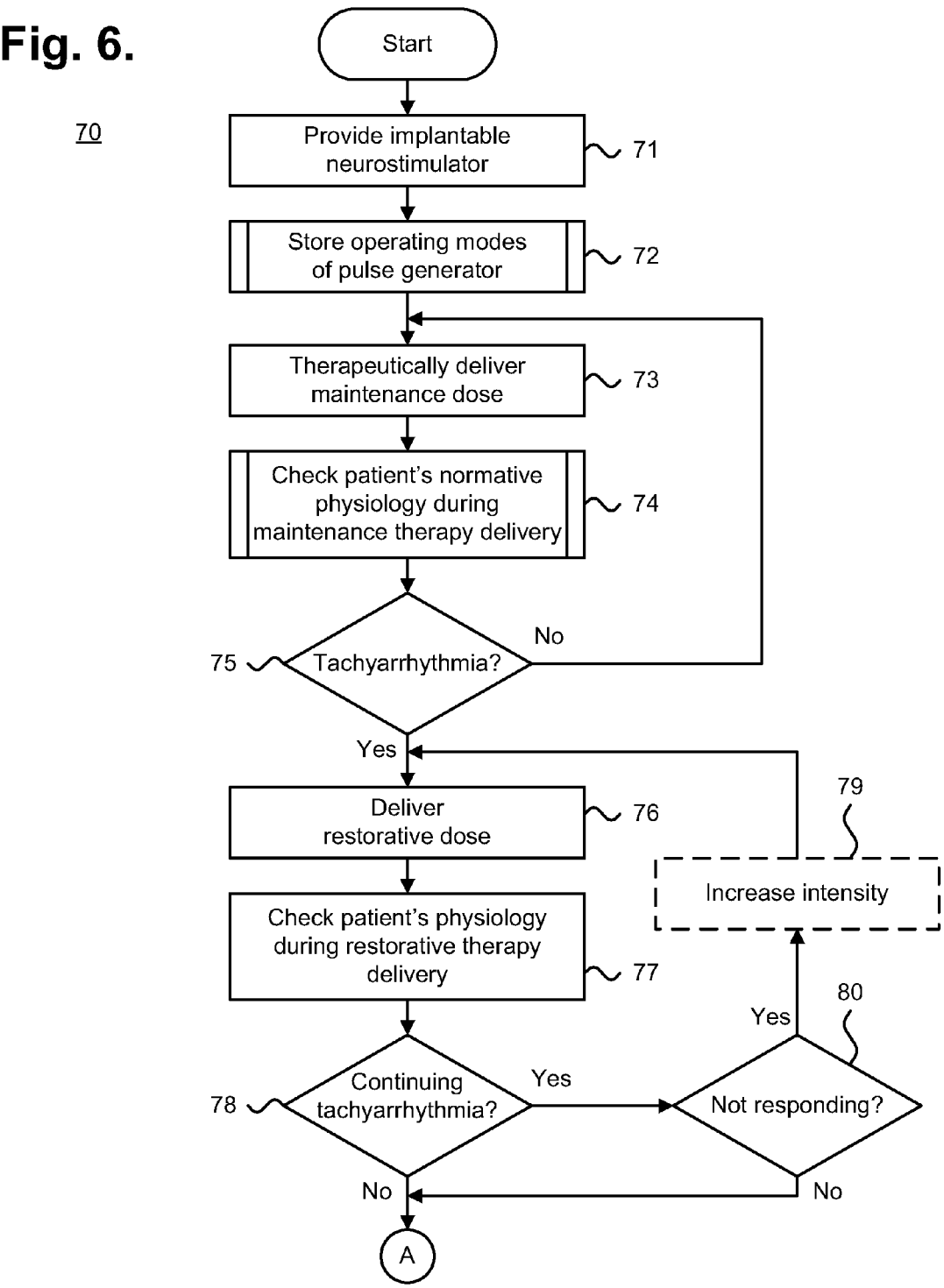
FIG. 6 is a flow diagram showing an implantable neurostimulator-implemented method for managing tachyarrhythmias through vagus nerve stimulation, in accordance with one embodiment.

Therapeutic maintenance dose VNS therapy can be suspended upon the occurrence of tachyarrhythmia and replaced with the delivery of higher intensity VNS that is tuned to prevent initiation of or disrupt tachyarrhythmia, after which therapy only resumes if tachyarrhythmia does not recur. FIG. 6 is a flow diagram showing an implantable neurostimulator-implemented method for managing tachyarrhythmias through vagus nerve stimulation 70, in accordance with one embodiment. The method is implemented on the stimulation device 11, the operation of which is parametrically defined through stored stimulation parameters and timing cycles.

Preliminarily, an implantable neurostimulator 12 with an integrated heart rate sensor 31, which includes a pulse generator 11, a nerve stimulation therapy lead 13, and a pair of helical electrodes 14, is provided (step 71). In an alternative embodiment, electrodes may be implanted with no implanted neurostimulator or leads. Power may be provided to the electrodes from an external power source and neurostimulator through wireless RF or inductive coupling. Such an embodiment may result in less surgical time and trauma to the patient. Furthermore, the integrated heart rate sensor 31 could be omitted in lieu of other types of sensing mechanisms for measuring the patient's physiology.

The pulse generator stores a set of operating modes (step 72) that parametrically defines both a low level maintenance dose and a high level restorative dose of the stimulation, as further described infra with reference to FIG. 7. Therapeutic VNS, as parametrically defined by the maintenance dose operating mode, is delivered to at least one of the vagus nerve (step 73). The pulse generator 11 delivers electrical therapeutic stimulation to the cervical vagus nerve of a patient 10 in a manner that results in creation and propagation (in both afferent and efferent directions) of action potentials within neuronal fibers of either the left or right vagus nerve 15, 16 independent of cardiac cycle.

Figure 8:
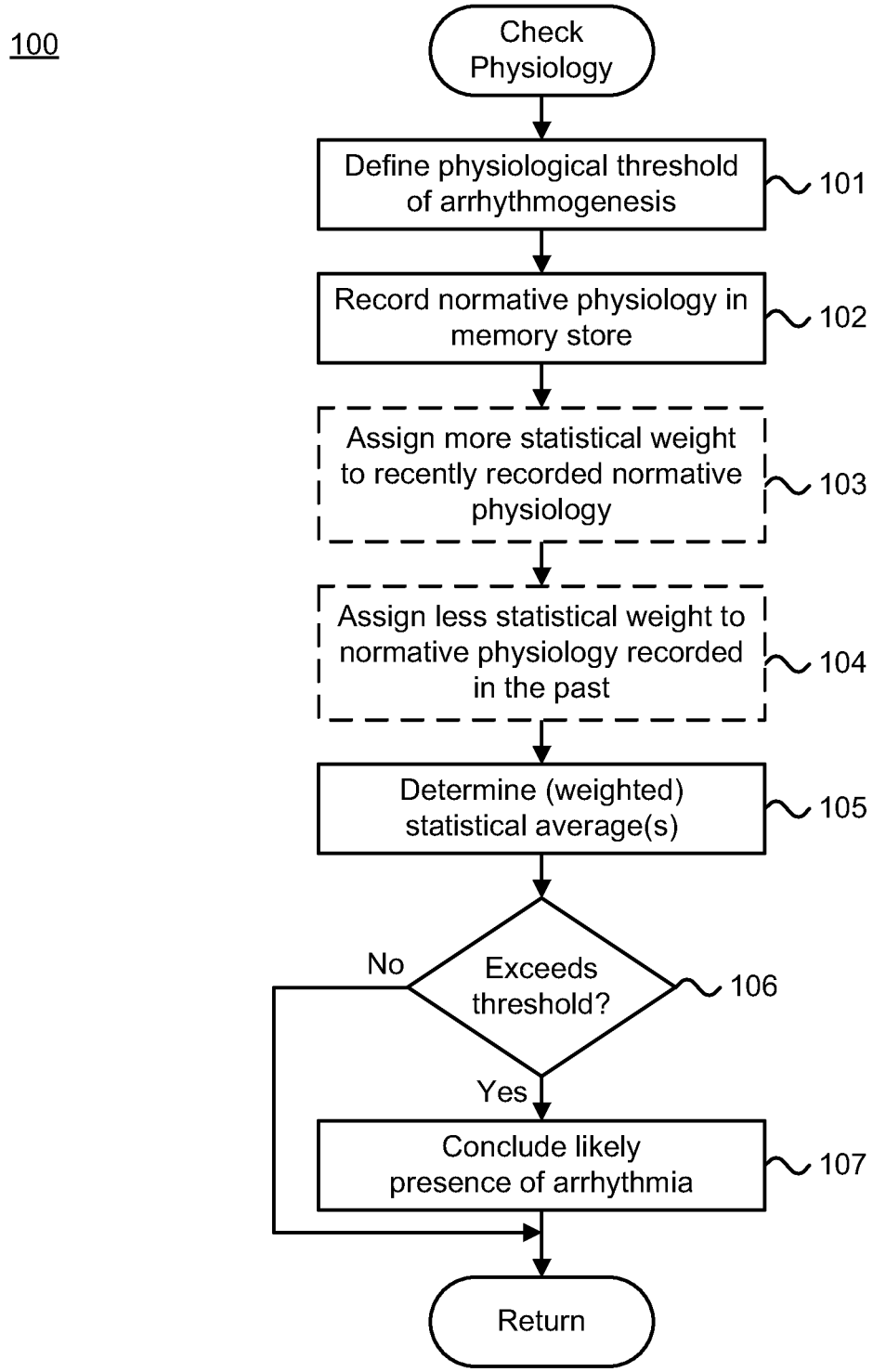
FIG. 8 is a flow diagram showing an optional routine for determining an onset or presence of arrhythmia with a recency filter for use with the method of FIG. 6.

During maintenance dose therapy delivery, the patient's normative physiology, which is physiology during normal sinus rhythm, is checked for tachyarrhythmias (step 74), as further described infra with reference to FIGS. 7 and 8. In general, the onset or presence of pathological tachyarrhythmia can be determined by heart rate or normal sinus rhythm through an endocardial electrogram, as well as rhythm stability, onset characteristics, and similar rate and rhythm morphological indicators, as conventionally used in cardiac rhythm management devices, such as described in K. Ellenbogen et al., "Clinical Cardiac Pacing and Defibrillation," Ch. 3, pp. 68-126 (2d ed. 2000), the disclosure of which is incorporated by reference. QRS complex alone may be insufficient to identify a specific type of tachyarrhythmia. A heart rate in excess of 100 bpm, for instance, can indicate the onset of tachyarrhythmia. Notwithstanding, while a narrow QRS complex usually indicates SVT tachycardia, a wide QRS complex can indicate any form of tachycardia, including VT tachycardia, as well as SVT and sinus tachycardia, and other indicia of tachycardia or tachyarrhythmia may be necessary before concluding that a change in therapeutic maintenance dose delivery is appropriate. For example, a wide QRS complex combined with a heart rate between around 120 bpm to 250 bpm strongly indicates the presence of VT. In a further embodiment, the onset or presence of arrhythmias, particularly VT, can be determined with the assistance of a recency filter, as further described supra with reference to FIG. 8. Still other physiological measures and indications of tachyarrhythmias are possible.

If a monitored physiological condition is indicative of tachyarrhythmia, that is, the patient's physiology indicates the onset or presence of tachyarrhythmia (step 75), the delivery of the maintenance dose is suspended and replaced with the delivery of a restorative dose of higher intensity VNS that is tuned to prevent initiation of or disrupt tachyarrhythmia (step 76). The patient's physiology is periodically monitored during the delivery of the restorative dose (step 77), the delivery of which is maintained (steps 76-77) while the tachyarrhythmia condition continues (step 78). If, after multiple checks of the patient's physiology (step 77), the arrhythmia is not responding to the delivery of the restorative dose (step 76), absent an improvement in heart rhythm, such as a decrease in the rate of the arrhythmia (step 77), restorative dose delivery is discontinued and treatment reverts to delivering the maintenance dose (step 81) after a set period of time following the termination of the arrhythmia (step 78).

In a further embodiment, delivery of the restorative dose can be manually suspended by providing the neurostimulator 12 with a magnetically-actuated reed switch that suspends delivery of the maintenance dose and resume delivery of the restorative dose, such as when the maintenance dose is tolerable to the patient 10, while the restorative dose is intolerable.

In a still further embodiment, the intensity of the restorative dose can be increased as necessary (step 80). For non-life-threatening or non-paroxysmal tachyarrhythmias, the intensity of the restorative dose is progressively increased, while for life-threatening or paroxysmal arrhythmias, a strong restorative dose of significantly higher intensity is used right away, due to the lack of time to ramp up the intensity progressively.

The recordable memory 29 in the electronic circuitry 22 of the neurostimulator 12 (shown in FIG. 2A) stores the stimulation parameters that control the overall functionality of the pulse generator 11 in providing VNS therapy. FIG. 7 is a flow diagram showing a routine 90 for storing operating modes for use with the method 70 of FIG. 6. Two operating modes are stored, which include a maintenance dose of VNS tuned to restore cardiac autonomic balance (step 91) through continuously-cycling, intermittent and periodic electrical pulses and a restorative dose tuned to prevent initiation of or disrupt tachyarrhythmia (step 92) through periodic electrical pulses delivered at higher intensity than the maintenance dose.

In one embodiment, the autonomic regulation therapy is provided in a low level maintenance dose independent of cardiac cycle to activate both parasympathetic afferent and efferent nerve fibers in the vagus nerve simultaneously and a high level restorative dose. In the maintenance dose, a pulse width in the range of 250 to 500 µsec delivering between 0.02 and 1.0 mA of output current at a signal frequency in the range of 10 to 20 Hz, and a duty cycle of 5 to 30%, although other therapeutic values could be used as appropriate.

Different restorative doses are provided in response to different tachyarrhythmias. The restorative dose settings are physician-programmable. For a default restorative dose, the stimulation parameters would be in the same range as the maintenance dose, but would be moderately higher, with a pulse width again in the range of 250 to 500 µsec delivering between 1.5 and 2.0 mA of output current at a signal frequency in the range of 10 to 20 Hz. The duty cycle may change significantly from nominally 10% to temporarily 50% or 100%, although other therapeutic values could be used as appropriate. In addition, for non-life-threatening or non-paroxysmal tachyarrhythmias, the intensity of the restorative dose is progressively increased over time by increasing output current, duty cycle, or frequency, lengthening pulse width, or through a combination of the foregoing parameters. As well, discretely-defined restorative doses, each using different sets of parameters, may be delivered in the course of treating a single continuing tachyarrhythmic event, such as for life-threatening or paroxysmal arrhythmias that rapidly generate and require a significantly stronger restorative dose with no ramp up time.

The physiology of the patient 10 is monitored during the delivery of the maintenance dose and while undertaking rehabilitative measures, such as restorative dose delivery to counter an occurrence of arrhythmia, particularly VT, or other significant increase, decrease, or entrainment of cardiac rhythm. FIG. 8 is a flow diagram showing an optional routine 100 for determining an onset or presence of arrhythmias with a recency filter for use with the method 70 of FIG. 6. Normative physiology refers to the relative physiology of a patient suffering from CHF or other form of chronic cardiac dysfunction and the physiology of a particular CHF patient may vary from the norm as observed in a healthy non-CHF individual. Physiological thresholds of arrhythmogenesis are defined (step 101) that are used to establish conditions that indicate a departure from normal sinus rhythm. Periodically, the normative physiology of the patient 10 is recorded in the recordable memory 29 (shown in FIG. 2A) (step 102). The normative physiology can include heart rate or normal sinus rhythm, as sensed by a physiological sensor, such as a heart rate monitor 31, as well as other available physiological data, for instance, as derivable from an endocardial electrogram. In a further embodiment, statistics can be stored in the recordable memory 29 for storage efficiency, instead of the raw sensed heart rate data. For instance, a binned average heart rate could be stored as representative of the patient's overall heart rate during a fixed time period. Based on the recorded normative physiology, a statistical average can be determined (step 105). If the statistical average exceeds the arrhythmogenic threshold (step 106), arrhythmia likely is present (step 107) and modification of the operating mode of the pulse generator 11 is indicated. The arrhythmia can include various forms of tachyarrhythmia, including atrial fibrillation (AF), ventricular tachyarrhythmias (ventricular tachycardia (VT) and ventricular fibrillation (VF)), and atrial flutter, and bradyarrhythmia, including atrial bradycardia, atrioventricular bradycardia, and ventricular bradycardia.

In a further embodiment, a form of recency filter is used to statistically favor recent events. By way of example, more statistical weight can be assigned to recently recorded normative physiology (step 103) and less statistical weight can be assigned to normative physiology recorded in the past (step 104). The lower weighting of older physiology values helps form a long-term running average that can be treated as a trailing baseline. A sliding window of physiology values collected, for example, over the past week can be applied to typify current patient condition. Weighted statistical averages are determined for recent and past normative physiology (step 105) and recent (foreground) and past (background or trailing) physiology averages can be compared (step 106) to identify arrhythmogenesis or other consideration.

In a still further embodiment, the sensed heart rate data can be used to analyze therapeutic efficacy and patient condition. For instance, statistics could be determined from the sensed heart rate, either onboard by the neurostimulator 12 or by an external device, such as a programming computer following telemetric data retrieval. The sensed heart rate data statistics can include determining a minimum heart rate over a stated time period, a maximum heart rate over a stated time period, an average heart rate over a stated time period, and a variability of heart rate over a stated period, where the stated period could be a minute, hour, day, week, month, or other selected time interval. Still other uses of the heart rate sensor 31 and the sensed heart rate data are possible In still further embodiments, the suspension and resumption of either or both the delivery of the maintenance dose and the restorative dose can be titrated to gradually withdraw or introduce their respective forms of VNS. As well, both forms of VNS therapy delivery can be manually suspended by providing the neurostimulator 12 with a magnetically-actuated reed switch that suspends delivery of the maintenance dose and the restorative dose, as applicable, in response to a remotely applied magnetic signal.

While the invention has been particularly shown and described as referenced to the embodiments thereof, those skilled in the art will understand that the foregoing and other changes in form and detail may be made therein without departing from the spirit and scope.

What is claimed is:

1. An implantable neurostimulator for managing tachyarrhythmias through vagus nerve stimulation, comprising:
   a pulse generator configured to couple to an electrode assembly and to generate electrical stimulation;
   a processor configured to receive physiological data from a physiological sensor; and
   a memory having instructions stored thereon that, when executed by the processor, cause the processor to:
      store operating modes of the pulse generator in the memory, by:
         defining a maintenance dose of the electrical stimulation having a duty cycle ranging from about four percent to about thirty six percent; and
         defining a restorative dose of the electrical therapeutic stimulation comprising electrical pulses delivered at higher intensity than the maintenance dose;
      deliver the maintenance dose at the duty cycle via the pulse generator to the electrode assembly, prior to delivering the restorative dose, prior to sensing a condition of tachyarrhythmia, and independent of cardiac cycle;
      monitor a patient's normative physiology to sense the condition of tachyarrhythmia via the processor receiving the physiological data; and
      upon sensing the condition of tachyarrhythmia, switch from delivering the maintenance dose to delivering the restorative dose at a higher duty cycle than the duty cycle of the maintenance dose to the electrode assembly via the pulse generator.

2. The implantable neurostimulator of claim 1, wherein the instructions further cause the processor to:
   record the patient's normative physiology in the memory;
   determine a statistical average of the patient's normative physiology recorded in the memory; and
   define the condition of tachyarrhythmia as triggered when the statistical average exceeds a physiological threshold of arrhythmogenesis.

3. The implantable neurostimulator of claim 2, wherein the instructions further cause the processor to:
   assign more statistical weight to a first portion of the patient's normative physiology that has been recorded recently;
   assign less statistical weight to a second portion of the patient's normative physiology that has been recorded less recently; and
   determine the statistical average as a weighted average of the patient's normative physiology.

4. The implantable neurostimulator of claim 1, wherein the instructions further cause the processor to:
   during monitoring, confirm that the patient's normative physiology comprises a normal sinus rhythm; and
   upon departure from the normal sinus rhythm, modify the operating mode of the pulse generator based on whether the departure signifies an increase, decrease, or entrainment of cardiac rhythm.

5. The implantable neurostimulator of claim 1, wherein the instructions further cause the processor to:
   construct an endocardial electrogram based on the patient's normative physiology;
   evaluate cardiac rate dynamics from the endocardial electrogram, including identifying R-waves; and
   define the condition of tachyarrhythmia as triggered when the R-waves exhibit significant irregularity over a fixed time period.

6. The implantable neurostimulator of claim 1, wherein the instructions further cause the processor to:
   specify one or more physiological markers of abnormally fast sinus rhythm as indicative of tachyarrhythmia;
   monitor the patient's sinus rhythm via the physiological sensor; and
   upon sensing at least one physiological marker of abnormally fast sinus rhythm, trigger delivery of the restorative dose.

7. The implantable neurostimulator of claim 1, further comprising the physiological sensor, wherein said physiological sensor comprises:
   a leadless heart rate sensor coupled to the pulse generator to sense a heart rate of the patient in response to the electrical therapeutic stimulation,
   wherein the instructions further cause the processor to:

specify a threshold heart rate as indicative of tachyarrhythmia;

monitor the heart rate of the patient through the leadless heart rate sensor; and upon sensing the heart rate of the patient is above the threshold heart rate, trigger the delivery of the restorative dose.

8. A non-transitory computer-readable medium comprising instructions executable by a processor of an implantable medical device to perform operations, the implantable medical device further comprising a pulse generator and a physiological sensor, the operations comprising:

storing operating modes of the pulse generator of the implantable medical device in the non-transitory computer-readable medium, by:

defining a maintenance dose of an electrical stimulation having a duty cycle ranging from about four percent to about thirty six percent; and defining a restorative dose of the electrical stimulation comprising electrical pulses delivered at higher intensity than the maintenance dose;

delivering, using the pulse generator, the maintenance dose at the duty cycle, prior to delivering the restorative dose, prior to sensing a condition of tachyarrhythmia, and independent of cardiac cycle;

monitoring a patient's normative physiology to sense the condition of tachyarrhythmia via the physiological sensor; and upon sensing the condition of tachyarrhythmia, switching from delivering the maintenance dose to delivering the restorative dose at a higher duty cycle than the duty cycle of the maintenance dose.

9. The non-transitory computer-readable medium of claim 8, wherein the operations further comprise:

recording the patient's normative physiology;

determining a statistical average of the patient's normative physiology recorded; and defining the condition of tachyarrhythmia as triggered when the statistical average exceeds a physiological threshold of arrhythmogenesis.

10. The non-transitory computer-readable medium of claim 9, wherein the operations further comprise:

assigning more statistical weight to a first portion of the patient's normative physiology that has been recorded recently;

assigning less statistical weight to a second portion of the patient's normative physiology that has been recorded less recently; and determining the statistical average as a weighted average of the patient's normative physiology.

11. The non-transitory computer-readable medium of claim 8, wherein the operations further comprise:

during monitoring, confirming that the patient's normative physiology comprises a normal sinus rhythm; and upon departure from the normal sinus rhythm, modifying the operating mode of the pulse generator based on whether the departure signifies an increase, decrease, or entrainment of cardiac rhythm.

12. The non-transitory computer-readable medium of claim 8, wherein the operations further comprise:

constructing an endocardial electrogram based on the patient's normative physiology;

evaluating cardiac rate dynamics from the endocardial electrogram, including identifying R-waves; and defining the condition of tachyarrhythmia as triggered when the R-waves exhibit significant irregularity over a fixed time period.

13. The non-transitory computer-readable medium of claim 8, wherein the operations further comprise:

specifying one or more physiological markers of abnormally fast sinus rhythm as indicative of tachyarrhythmia;

monitoring the patient's sinus rhythm via the physiological sensor; and upon sensing at least one physiological marker of abnormally fast sinus rhythm, triggering delivery of the restorative dose.

14. The non-transitory computer-readable medium of claim 8, wherein the operations further comprise specifying:

a threshold heart rate as indicative of tachyarrhythmia, monitoring the patient's normative physiology to sense the condition of tachyarrhythmia comprises monitoring the heart rate of the patient, and delivery of the restorative dose is triggered in response to sensing the heart rate of the patient is above the threshold heart rate.

15. A method for managing tachyarrhythmias through vagus nerve stimulation, comprising:

storing operating modes for a pulse generator of an implantable medical device within a memory of the implantable medical device by:

defining a maintenance dose of an electrical stimulation having a duty cycle ranging from about four percent to about thirty six percent; and defining a restorative dose of the electrical stimulation comprising electrical pulses delivered at higher intensity than the maintenance dose;

delivering, using the pulse generator, the maintenance dose at the duty cycle, prior to delivering the restorative dose, prior to sensing a condition of tachyarrhythmia, and independent of cardiac cycle;

monitoring, using a sensor, a patient's normative physiology to sense the condition of tachyarrhythmia; and upon sensing the condition of tachyarrhythmia, switching from delivering the maintenance dose to delivering the restorative dose at a higher duty cycle than the duty cycle of the maintenance dose.

16. The method of claim 15, further comprising:

recording the patient's normative physiology;

determining a statistical average of the patient's normative physiology recorded; and defining the condition of tachyarrhythmia as triggered when the statistical average exceeds a physiological threshold of arrhythmogenesis.

17. The method of claim 16, further comprising:

assigning more statistical weight to a first portion of the patient's normative physiology that has been recorded recently;

assign less statistical weight to a second portion of the patient's normative physiology that has been recorded less recently; and determining the statistical average as a weighted average of the patient's normative physiology.

18. The method of claim 15, further comprising:

during monitoring, confirming that the patient's normative physiology comprises a normal sinus rhythm; and upon departure from the normal sinus rhythm, modifying the operating mode of the pulse generator based on whether the departure signifies an increase, decrease, or entrainment of cardiac rhythm.

19. The method of claim 15, further comprising:

constructing an endocardial electrogram based on the patient's normative physiology;

evaluating cardiac rate dynamics from the endocardial electrogram, including identifying R-waves; and defining the condition of tachyarrhythmia as triggered when the R-waves exhibit significant irregularity over a fixed time period.

20. The method of claim 15, further comprising:

specifying a threshold heart rate as indicative of tachyarrhythmia, wherein monitoring the patient's normative physiology to sense the condition of tachyarrhythmia comprises monitoring the heart rate of the patient, and wherein delivery of the restorative dose is triggered in response to sensing the heart rate of the patient is above the threshold heart rate.

* * * * *